US012674136B2

(12) United States Patent
Li et al.

(10) Patent No.: US 12,674,136 B2
(45) Date of Patent: Jul. 7, 2026

(54) METHODS FOR PREPARING TUMOR-INFILTRATING LYMPHOCYTES

(71) Applicant: SHANGHAI ABELZETA LTD., Shanghai (CN)

(72) Inventors: Jia Li, Shanghai (CN); Jiyan Hou, Shanghai (CN); Zizhen Gong, Shanghai (CN); Yijie Qu, Shanghai (CN); Shichao Qin, Shanghai (CN); Shenchen Wang, Shanghai (CN); Wangqin Shu, Shanghai (CN); Junfeng Wu, Shanghai (CN); Fei Wang, Shanghai (CN); Li Zhang, Shanghai (CN)

(73) Assignee: Shanghai AbelZeta Ltd., Shanghai (CN)

( * ) Notice: Subject to any disclaimer, the term of this patent is extended or adjusted under 35 U.S.C. 154(b) by 594 days.

(21) Appl. No.: 18/259,611

(22) PCT Filed: Dec. 29, 2021

(86) PCT No.: PCT/CN2021/142540
§ 371 (c)(1),
(2) Date: Jun. 28, 2023

(87) PCT Pub. No.: WO2022/143785
PCT Pub. Date: Jul. 7, 2022

(65) Prior Publication Data
US 2024/0060041 A1 Feb. 22, 2024

(30) Foreign Application Priority Data

Dec. 31, 2020 (CN) .......................... 202011629408.7

(51) Int. Cl.
| | |
|---|---|
| *C12N 5/078* | (2010.01) |
| *A61K 40/11* | (2025.01) |
| *A61K 40/42* | (2025.01) |
| *A61P 35/00* | (2006.01) |
| *C12N 5/0783* | (2010.01) |

(52) U.S. Cl.
CPC ............ *C12N 5/0634* (2013.01); *A61K 40/11* (2025.01); *A61K 40/42* (2025.01); *A61P 35/00* (2018.01); *C12N 5/0636* (2013.01); *C12N 5/0638* (2013.01); *C12N 2501/2302* (2013.01); *C12N 2501/2307* (2013.01); *C12N 2501/2315* (2013.01); *C12N 2501/2321* (2013.01); *C12N 2501/73* (2013.01); *C12N 2501/734* (2013.01)

(58) Field of Classification Search
CPC .................................................... C12N 5/0634
See application file for complete search history.

(56) References Cited

U.S. PATENT DOCUMENTS

| | | | |
|---|---|---|---|
| 10,420,799 | B2 | 9/2019 | Wardell et al. |
| 2019/0276802 | A1 | 9/2019 | Simpson-Abelson et al. |
| 2020/0338125 | A1 | 10/2020 | Bobisse et al. |

FOREIGN PATENT DOCUMENTS

| | | |
|---|---|---|
| CN | 103396991 A | 11/2013 |
| CN | 110042080 A | 7/2019 |
| CN | 110099998 A | 8/2019 |
| CN | 110199016 A | 9/2019 |
| CN | 111040995 A | 1/2020 |
| CN | 110785486 A | 2/2020 |
| CN | 111286486 A | 6/2020 |
| CN | 111801415 A | 10/2020 |
| JP | 2019534030 A | 11/2019 |
| JP | 2020515257 A | 5/2020 |
| WO | 2018/204761 A1 | 11/2018 |
| WO | 2019/190579 A1 | 10/2019 |
| WO | 2019/210131 A1 | 10/2019 |
| WO | 2020/096988 A2 | 5/2020 |

OTHER PUBLICATIONS

International Search Report and Written Opinion of PCT/CN2021/142540, mailed Mar. 30, 2022.
Baldan et al. Efficient and reproducible generation of tumour-infiltrating lymphocytes for renal cell carcinoma. Br J Cancer 112, 1510-1518 (2015).
Friedman et al. Augmented lymphocyte expansion from solid tumors with engineered cells for costimulatory enhancement. J Immunother. 2011; 34(9):651-661.
Lee et al., Expansion of tumor-infiltrating lymphocytes and their potential for application as adoptive cell transfer therapy in human breast cancer. Oncotarget. 2017; 8(69):113345-113359.
Ye et al., CD137 accurately identifies and enriches for naturally occurring tumor-reactive T cells in tumor. Clin Cancer Res. 2014, 20(1):44-55.
Yunger et al., Tumor-infiltrating lymphocytes from human prostate tumors reveal anti-tumor reactivity and potential for adoptive cell therapy, OncoImmunology, (2019) 8(12): e1672494.

*Primary Examiner* — Prema M Mertz
(74) *Attorney, Agent, or Firm* — LEASON ELLIS LLP

(57) ABSTRACT

Provided are methods for expanding tumor-infiltrating lymphocytes (TILs), which include co-culturing an initial cell population containing TILs with first feeder cells to obtain a first expanded cell population; and then co-culturing the first expanded cell population with second feeder cells to obtain an expanded TIL population. The methods can quickly produce a large number of TILs from a small tumor sample.

9 Claims, 6 Drawing Sheets tumor sample
obtained from
patient

Dissociate to single cells;
Add cytokines to
stimulate overnight

First expansion:
add feeder cells, cytokines
and antibodies

Cryopreservation

Direct expansion

Second expansion: add
feeder cells, cytokines and
antibodies

Cell numbers before and after cryopreservation

Cell viabilities (%) before and after cryopreservation

Cell ratios (%) before and after cryopreservation

METHODS FOR PREPARING TUMOR-INFILTRATING LYMPHOCYTES

CROSS REFERENCE TO RELATED APPLICATION

The present application claims priority to Chinese patent application No. 2020116294087, filed on Dec. 31, 2020, which is hereby incorporated by reference in its entirety.

TECHNICAL FIELD

The present disclosure relates to the field of biotechnology, and in particular to a method for preparing tumor-infiltrating lymphocytes (TILs).

BACKGROUND

In recent years, considerable progress has been made in cancer immunotherapy. In cellular immunotherapy, also known as adoptive cell therapy, a patient's immune cells are collected for genetic modification or selective expansion to enhance the antigen-specific immune responses.

T cell adoptive reinfusion therapy mainly comprises using CAR-T, TCR-T and TIL. CAR-T is effective in the treatment of hematoma but its efficacy in treating solid tumors still needs to be improved. The effectiveness of TIL in the treatment of solid tumors has been studied in many aspects since the results of the melanoma clinical trials were first disclosed. TIL clinical trials have been extended to treating lung cancer, cervical cancer, head and neck cancer and others. However, one of the limitations is that TILs have be obtained from cancer tissues and the culture time for expansion is relatively long. This makes it difficult to obtain sufficient number of TIL cells to treat patients with inoperable cancers.

The existing TIL expansion methods mainly start from large tumor tissues. A large number of TILs are required for successful immunotherapy. This has been a challenge to achieve because of technical and logistical issues with cell expansion. It is especially challenging to expand TILs from patients whose surgical samples are difficult to obtain. Current TIL manufacturing processes are also limited by length, cost, and other factors.

There is an urgent need to provide efficient and rapid TIL expansion processes, especially starting from very small tumor samples or samples containing a small number of TILs.

SUMMARY

The present disclosure provides methods that can quickly obtain a large number of TILs from a very small tumor sample or a small number of starting TIL cells.

The present disclosure provides a method for expanding or preparing tumor-infiltrating lymphocytes (TILs) in vitro. The method may comprise:

(1) providing an initial cell population containing TILs from a sample, wherein the number of TILs in the initial cell population is n0;

(2) optionally pre-treating the initial cell population, the pretreatment comprising culturing the initial cell population with IL7, IL15 and/or IL21 for about 6 hours to about 36 hours, for about 6 hours to about 48 hours, for about 6 hours to about 12 hours, for about 6 hours to about 24 hours, for about 12 hours to about 36 hours, for about 24 hours to about 36 hours, or for about 24 hours to about 48 hours, to obtain a pretreated initial cell population;

(3) co-culturing the initial cell population, or the pretreated initial cell population, with first feeder cells in a first culture medium for a first period, to obtain a first expanded cell population, wherein the number of TILs in the first expanded cell population is n1; and (4) co-culturing the first expanded cell population with second feeder cells in a second culture medium for a second period, to obtain an expanded TIL population, wherein the number of TILs in the expanded TIL population is n2.

As described herein, step (3) is referred to as the first expansion or first TIL expansion. Step (4) is referred to as the second expansion or second TIL expansion.

The first period may range from about 7 days to about 16 days, from about 8 days to about 16 days, from about 9 days to about 16 days, from about 10 days to about 16 days, from about 11 days to about 16 days, from about 12 days to about 16 days, from about 7 days to about 14 days, from about 8 days to about 14 days, from about 9 days to about 14 days, from about 10 days to about 14 days, from about 11 days to about 14 days, or from about 12 days to about 14 days.

The second period may range from about 10 days to about 16 days, from about 8 days to about 16 days, from about 9 days to about 16 days, from about 11 days to about 16 days, from about 12 days to about 16 days, from about 8 days to about 14 days, from about 9 days to about 14 days, from about 10 days to about 14 days, from about 11 days to about 14 days, or from about 12 days to about 14 days.

The sample may be a tumor sample. The tumor sample may be from a solid tumor, such as lung cancer, cervical cancer, ovarian cancer, or melanoma.

The sample may have a weight ranging from about 0.01 g to about 0.5 g, from about 0.01 g to about 0.4 g, from about 0.01 g to about 0.3 g, from about 0.01 g to about 0.2 g, from about 0.01 g to about 0.1 g, from about 0.01 g to about 0.09 g, from about 0.01 g to about 0.08 g, from about 0.01 g to about 0.07 g, from about 0.01 g to about 0.06 g, from about 0.01 g to about 0.05 g, about 0.01 g, about 0.02 g, about 0.03 g, about 0.04 g or about 0.05 g.

The number of TILs in the initial cell population, n0, may range from about 1,000 to about 50,000, from about 2,000 to about 50,000, from about 3,000 to about 50,000, from about 4,000 to about 50,000, from about 5,000 to about 50,000, from about 1,000 to about 30,000, from about 2,000 to about 30,000, from about 3,000 to about 30,000, from about 4,000 to about 30,000, from about 5,000 to about 30,000, from about 1,000 to about 10,000, from about 2,000 to about 10,000, from about 3,000 to about 10,000, about 4,000 to about 10,000, or from about 5,000 to about 10,000.

$N1/n0$ may range from about 1,000 to about 10,000, from about 2,000 to about 10,000, from about 3,000 to about 10,000, from about 4,000 to about 10,000, from about 5,000 to about 10,000, from about 6,000 to about 10,000, from about 7,000 to about 10,000, or from about 8,000 to about 10,000.

The number of TILs in the first expanded cell population, n1, may be at least or about $1 \times 10^7$, at least or about $0.1 \times 10^7$, at least or about $0.3 \times 10^7$, at least or about $0.5 \times 10^7$, at least or about $0.7 \times 10^7$, at least or about $0.9 \times 10^7$, at least or about $1.5 \times 10^7$, at least or about $2 \times 10^7$, at least or about $2.5 \times 10^7$, at least or about $3 \times 10^7$, at least or about $3.5 \times 10^7$, at least or about $4 \times 10^7$, at least or about $4.5 \times 10^7$, at least or about $5 \times 10^7$, at least or about $6 \times 10^7$, at least or about $7 \times 10^7$, at least or about $8 \times 10^7$, at least or about $9 \times 10^7$, at least or about $1 \times 10^8$, at least or about $1.5 \times 10^8$, at least or about $2 \times 10^8$, at least or about $2.5 \times 10^8$, at least or about $3 \times 10^8$, at least or about $3.5 \times 10^8$, at least or about $4 \times 10^8$, at least or about $4.5 \times 10^8$, at least or about $5 \times 10^8$, at least or about $6 \times 10^8$, at least or about $7 \times 10^8$, at least or about $8 \times 10^8$, or at least or about $9 \times 10^8$. In certain embodiments, n1 is about $0.1 \times 10^8$ to about $3.0 \times 10^8$, or about $0.3 \times 10^8$ to about $2.0 \times 10^8$.

In certain embodiments, n1/n0 ranges from about 1000 to about 10,000, and n1 is at least $1 \times 10^7$.

The number of TILs in the second expanded cell population, n2, may be at least or about $1 \times 10^{10}$, at least or about $0.1 \times 10^{10}$, at least or about $0.3 \times 10^{10}$, at least or about $0.5 \times 10^{10}$, at least or about $0.7 \times 10^{10}$, at least or about $0.9 \times 10^{10}$, at least or about $1.5 \times 10^{10}$, at least or about $2 \times 10^{10}$, at least or about $2.5 \times 10^{10}$, at least or about $3 \times 10^{10}$, at least or about $3.5 \times 10^{10}$, at least or about $4 \times 10^{10}$, at least or about $4.5 \times 10^{10}$, at least or about $5 \times 10^{10}$, at least or about $6 \times 10^{10}$, at least or about $7 \times 10^{10}$, at least or about $8 \times 10^{10}$, at least or about $9 \times 10^{10}$, at least or about $1 \times 10^{11}$, at least or about $1.5 \times 10^{11}$, at least or about $2 \times 10^{11}$, at least or about $2.5 \times 10^{11}$, at least or about $3 \times 10^{11}$, at least or about $3.5 \times 10^{11}$, at least or about $4 \times 10^{11}$, at least or about $4.5 \times 10^{11}$, at least or about $5 \times 10^{11}$, at least or about $6 \times 10^{11}$, at least or about $7 \times 10^{11}$, at least or about $8 \times 10^{11}$, or at least or about $9 \times 10^{11}$. In certain embodiments, n2 is about $1 \times 10^{10}$ to about $2 \times 10^{11}$. In certain embodiments, n2 is about $1.0 \times 10^{11}$ to about $2.0 \times 10^{11}$.

N2/n1 may range from about 1,000 to about 10,000, from about 2,000 to about 10,000, from about 3,000 to about 10,000, from about 4,000 to about 10,000, from about 5,000 to about 10,000, from about 6,000 to about 10,000, from about 7,000 to about 10,000, or from about 8,000 to about 10,000.

In certain embodiments, n2/n1 ranges from about 4000 to about 10,000, and n2 is at least $1 \times 10^{10}$.

The sample may be dissociated (e.g., in step (1)) with a dissociation solution to obtain the initial cell population. The dissociation solution may comprise an isotonic solution comprising collagenase II, collagenase IV, DNase, and hyaluronidase.

The first culture medium may comprise one or more cytokines selected from the group consisting of IL2, IL7, IL15, and IL21.

The concentration of IL2 in the first culture medium may range from about 300 IU/ml to about 10000 IU/ml, or as described herein.

In the first culture medium (e.g., in the first expansion, or in step (3)), in the second culture medium (e.g., in the second expansion, or in step (4)), or in the pre-treating step (e.g., step (2)), IL7, IL15, or IL21 may have a concentration ranging from about 10 ng/ml to about 100 μg/ml, about 1 ng/ml to about 100 μg/ml, about 20 ng/ml to about 100 μg/ml, about 50 ng/ml to about 100 μg/ml, about 100 ng/ml to about 100 μg/ml, about 500 ng/ml to about 100 μg/ml, about 1 μg/ml to about 100 μg/ml, about 10 μg/ml to about 100 μg/ml, about 50 μg/ml to about 100 μg/ml, about 10 ng/ml to about 50 μg/ml, about 50 ng/ml to about 50 μg/ml, about 100 ng/ml to about 50 μg/ml, about 500 ng/ml to about 50 μg/ml, about 1 μg/ml to about 50 μg/ml, about 10 μg/ml to about 50 μg/ml, about 50 ng/ml to about 10 μg/ml, about 100 ng/ml to about 10 μg/ml, about 200 ng/ml to about 10 μg/ml, about 500 ng/ml to about 10 μg/ml, about 1 μg/ml to about 10 μg/ml, about 10 ng/ml to about 1 μg/ml, about 100 ng/ml to about 1 μg/ml, about 200 ng/ml to about 1 μg/ml, about 500 ng/ml to about 1 μg/ml, or about 3 ng/ml to about 30 ng/ml.

The first expansion and the second expansion may be performed in the same culture container or in different culture containers. For example, the first expansion may be performed in a first culture container, and the second expansion may be performed in a second culture container.

The first culture medium may comprise one or more antibodies selected from an anti-CD3 antibody or fragments thereof, an anti-41BB antibody or fragments thereof, an anti-OX40 antibody or fragments thereof, and an anti-PD-1 antibody or fragments thereof.

The second culture medium may comprise an anti-CD3 antibody or fragments thereof, and/or an anti-CD28 antibody or fragments thereof.

The second culture medium may comprise microbeads coated with an anti-CD3 antibody or fragments thereof, and/or an anti-CD28 antibody or fragments thereof.

The anti-CD3 antibody or fragments thereof may be OKT3 antibody or fragments thereof. The first feeder cells and/or the second feeder cells may be antigen presenting cells.

The first feeder cells and/or the second feeder cells may be peripheral blood mononuclear cells (PBMCs).

The present disclosure also provides for tumor-infiltrating lymphocytes (TILs) prepared by the present method (e.g., the expanded TIL population).

Also encompassed by the present disclosure is a pharmaceutical composition comprising the TILs (e.g., after expansion, for example, the expanded TIL population).

The pharmaceutical composition may further comprise a pharmaceutically acceptable carrier.

The present disclosure also provides for a method of treating a disease in a patient, the method comprising administering the pharmaceutical composition or TILs to the patient.

The disease may be cancer.

A first aspect of the present disclosure provides a method for preparing TIL cells. The method may comprise:

(1) providing an initial cell population containing TIL cells from a tumor sample, wherein the number of TIL cells in the initial cell population is n0;

(2) optionally pre-treating the initial cell population, the pretreatment comprising culturing the initial cell population in the presence of IL7, IL15 and/or IL21 for about 6 hours to about 36 hours, about 8 hours to about 30 hours, or about 10 hours to about 24 hours, to obtain a pretreated initial cell population;

(3) co-culturing the initial cell population (or the pretreated initial cell population) and first feeder cells in a first culture medium for a period of time, t1, to obtain a first expanded cell population, wherein the number of TIL cells in the first expanded cell population is n1, where n1/n0 is about 1000 to about 10000, and n1≥1× $10^7$; and (4) co-culturing the first expanded cell population with second feeder cells in a second culture medium for a period of time, t2, to obtain a second expanded cell population (i.e., an expanded TIL population), wherein the number of TIL cells in the second expanded cell population is n2, where n2/n1 is about 4000 to about 10000, and n2≥1× $10^{10}$.

Step (3) can be carried out in a first culture container. Step (4) can be carried out in a second culture container. Step (3) and step (4) can be carried out in the same culture container.

In certain embodiments, t1 is about 7 days to about 16 days, or about 9 days to about 14 days.

In certain embodiments, t2 is about 10 days to about 16 days, or about 12 days to about 14 days.

In certain embodiments, based on a total number of cells in the second expanded cell population, the purity of the TIL cells in the second expanded cell population is at least or about 70%, at least or about 75%, at least or about 80%, at least or about 85%, at least or about 90%, at least or about 92%, at least or about 94%, at least or about 95% or higher.

In certain embodiments, a total expansion ratio $n2/n0$ of steps (3) and (4) is about $0.1 \times 10^7$ to about $20 \times 10^7$, or about $1 \times 10^7$ to about $10 \times 10^7$.

In certain embodiments, $n0$ is $\geq 2000$.

In certain embodiments, the first culture medium comprises a basal culture medium, serum or a serum substitute, and/or L-glutamine. In certain embodiments, the first culture medium comprises one or more cytokines selected from IL-2, IL-7, IL-15, and IL-21. In certain embodiments, the first culture medium comprises anti-CD3 antibody or fragments thereof (e.g., OKT3 antibody or fragments thereof), an anti-41BB antibody or fragments thereof, an anti-OX40 antibody or fragments thereof, an anti-PD-1 antibody or fragments thereof, or combinations thereof.

In certain embodiments, in the first expansion, at the beginning of the co-culturing, a cell number ratio R1 of the TIL cells in the initial cell population (or the pretreated initial cell population) to the first feeder cells ranges from about 1:10 to about 1:10000, about 1:10 to about 1:1000, about 1:10 to about 1:5000, about 1:20 to about 1:5000, about 1:10 to about 1:500, about 1:25 to about 1:500, about 1:25 to about 1:400, about 1:25 to about 1:300, about 1:25 to about 1:200, or about 1:25 to about 1:100.

In certain embodiments, in the second expansion, at the beginning of the co-culturing, a cell number ratio R2 of the TIL cells in the first expanded cell population to the second feeder cells ranges from about 1:2 to about 1:400, from about 1:2 to about 1:1,000, from about 1:2 to about 1:500, from about 1:2 to about 1:300, from about 1:2 to about 1:200, from about 1:2 to about 1:100, from about 1:5 to about 1:400, from about 1:5 to about 1:1,000, from about 1:5 to about 1:500, from about 1:5 to about 1:300, from about 1:5 to about 1:200, from about 1:5 to about 1:100, from about 1:10 to about 1:400, from about 1:10 to about 1:1,000, from about 1:10 to about 1:500, from about 1:10 to about 1:300, from about 1:10 to about 1:200, or from about 1:10 to about 1:100.

In certain embodiments, the tumor sample is an in vitro sample.

In certain embodiments, the tumor sample is a very small tumor sample or a sample containing a small number of starting TILs.

In certain embodiments, the tumor sample may be a biopsy sample such as an excisional biopsy sample, and an incisional biopsy sample. In certain embodiments, the tumor sample may be a tumor biopsy sample. In certain embodiments, the tumor sample may be an aspiration biopsy sample, such as a fine needle aspiration biopsy sample. In certain embodiments, the tumor sample may be a resected or dissected tumor sample. In certain embodiments, the tumor sample may be a puncture sample. In certain embodiments, the tumor sample may be a surgical sample.

In certain embodiments, the tumor sample is obtained from a tumor patient.

In certain embodiments, samples may be maintained in growth media with high-dose IL-2 (e.g., 6,000 IU/mL), and monitored for destruction of tumor and/or proliferation of TIL. Any tumor with viable cells remaining after processing can be enzymatically digested into a single cell suspension, and cryopreserved or be processed directly for expansion of TILs.

In certain embodiments, the TIL cells comprise a small number of starting cells obtained by a method such as selection for TILs after dissociation.

In certain embodiments, the tumor sample comprises but is not limited to a solid tumor such as lung cancer, cervical cancer, and ovarian cancer.

In certain embodiments, the tumor sample has a weight of about 0.01 g to about 0.05 g, about 0.01 g to about 0.05 g, about 0.02 g to about 0.04 g, about 0.01 g, about 0.02 g, about 0.03 g, about 0.04 g, or about 0.05 g.

In certain embodiments, the tumor sample has a weight of about 0.01 g to about 0.5 g, about 0.01 g to about 0.45 g, about 0.01 g to about 0.4 g, about 0.01 g to about 0.35 g, about 0.01 g to about 0.3 g, about 0.01 g to about 0.25 g, about 0.01 g to about 0.2 g, about 0.01 g to about 0.15 g, about 0.01 g to about 0.1 g, about 0.01 g to about 0.09 g, about 0.01 g to about 0.08 g, about 0.01 g to about 0.07 g, about 0.01 g to about 0.06 g, about 0.06 g, about 0.07 g, about 0.08 g, about 0.09 g, about 0.1 g, about 0.15 g, about 0.2 g, about 0.25 g, about 0.3 g, about 0.35 g, about 0.4 g, about 0.45 g, or about 0.5 g.

In certain embodiments, $n0$ is about 1,000 to about 50,000, about 2,000 to about 50,000, about 2,000 to about 10,000, or about 3,000 to about 10,000.

In certain embodiments, $n1$ is about $0.1 \times 10^8$ to about $3.0 \times 10^8$, or about $0.3 \times 10^8$ to about $2.0 \times 10^8$.

In certain embodiments, $n2$ is about $1 \times 10^{10}$ to about $2 \times 10^{11}$. In certain embodiments, $n2$ is about $1.0 \times 10^{11}$ to about $2.0 \times 10^{11}$.

One embodiment of the method further comprises enzymatically digesting the solid tumor tissue prior to (optionally isolating and) culturing the TILs.

In certain embodiments, the tumor sample may be dissociated with a dissociation solution to obtain the initial cell population containing TIL cells. The dissociation solution may comprise collagenase II, collagenase IV, DNase, hyaluronidase, and/or an isotonic solution.

In certain embodiments, the isotonic solution comprises but is not limited to a culture medium, Dulbecco's phosphate-buffered saline (DPBS) and the like.

In certain embodiments, in the dissociation solution, collagenase II has a concentration of about 0.1 g/ml to about 10 g/ml; collagenase IV has a concentration of about 0.1 g/ml to about 10 g/ml; the DNase has a concentration of about 0.1 g/ml to about 10 g/ml; and the hyaluronidase has a concentration of about 10 U/ml to about 1000 U/ml.

In certain embodiments, in the pretreating step (e.g., step (2)), in the first culture medium ((e.g., in step (3)), or in the second culture medium ((e.g., in step (4)), IL7 may have a concentration of about 10 ng/ml to about 100 μg/ml. IL15 may have a concentration of about 10 ng/ml to about 100 μg/ml. IL21 may have a concentration of about 10 ng/ml to about 100 μg/ml.

In certain embodiments, a cell number ratio of the TIL cells in the initial cell population to the first feeder cells may be about 1:10 to about 1:10000, about 1:100 to about 1:600, or about 1:200 to about 1:400.

In certain embodiments, the first culture medium contains one or more cytokines selected from IL-2, IL-7, IL-15, and IL-21. In certain embodiments, the first culture medium contains one or more antibodies selected from anti-CD3 antibody or fragments thereof (e.g., OKT3 antibody or fragments thereof), anti-41BB antibody or fragments thereof, anti-OX40 antibody or fragments thereof, and anti-PD-1 antibody or fragments thereof.

In certain embodiments, the first culture medium is a liquid culture medium.

In certain embodiments, the first culture medium is a complete culture medium.

In certain embodiments, in the first culture medium, OKT3 has a concentration of about 3 ng/ml to about 100 ng/ml.

In certain embodiments, in the first culture medium, or in the second culture medium, IL2 has a concentration of about 300 IU/ml to about 10,000 IU/ml, about 5,000 IU/ml to about 10,000 IU/ml, about 500 IU/ml to about 10,000 IU/ml, about 800 IU/ml to about 10,000 IU/ml, about 1,000 IU/ml to about 10,000 IU/ml, about 1,200 IU/ml to about 10,000 IU/ml, about 1,500 IU/ml to about 10000 IU/ml, about 1,800 IU/ml to about 10,000 IU/ml, about 2,000 IU/ml to about 10,000 IU/ml, about 3,000 IU/ml to about 10,000 IU/ml, about 4,000 IU/ml to about 10,000 IU/ml, about 5,000 IU/ml to about 10000 IU/ml, about 6,000 IU/ml to about 10,000 IU/ml, about 7,000 IU/ml to about 10000 IU/ml, about 8,000 IU/ml to about 10,000 IU/ml, about 9,000 IU/ml to about 10000 IU/ml, about 300 IU/ml to about 5,000 IU/ml, about 500 IU/ml to about 5,000 IU/ml, about 1,000 IU/ml to about 8,000 IU/ml, about 1,000 IU/ml to about 5,000 IU/ml, about 500 IU/ml, about 600 IU/ml, about 700 IU/ml, about 800 IU/ml, about 900 IU/ml, about 1,000 IU/ml, about 2,000 IU/ml, about 3,000 IU/ml, about 4,000 IU/ml, about 5,000 IU/ml, about 6,000 IU/ml, about 7,000 IU/ml, about 8,000 IU/ml, about 9,000 IU/ml, or about 10,000 IU/ml.

In certain embodiments, in the first expansion (e.g., step (3)), during the culturing process, a number of the TIL cells is controlled to be about 0.2 million cells/ml ($0.2 \times 10^6$ cells/10 to about 4 million cells/ml ($4 \times 10^6$ cells/ml).

In certain embodiments, the cell density is controlled by fluid/medium replacement or perfusion/infusion.

In certain embodiments, the first feeder cells are irradiated cells.

In certain embodiments, the feeder cells comprise but are not limited to peripheral blood mononuclear cells (PBMCs) and/or antigen presenting cells, etc. In certain embodiments, the feeder cells may comprise PBMC-derived feeder cells. In certain embodiments, the feeder cells may comprise artificial antigen-presenting cells developed from K562 cells (Forget et al., Activation and propagation of tumor infiltrating lymphocytes on clinical-grade designer artificial antigen presenting cells for adoptive immunotherapy of melanoma, J. Immunother. 2014, 37(9): 448-460; Lozzio etc., Human chronic myelogenous leukemia cell-line with positive Philadelphia chromosome, Blood. 1975, 45:321-334).

In some embodiments, the antigen-presenting cells are peripheral blood mononuclear cells (PBMCs). In some embodiments, the PBMCs are irradiated and allogeneic. In some embodiments, the antigen-presenting cells are artificial antigen-presenting cells.

In one embodiment, the feeder cells are irradiated PBMCs.

The first feeder cells and the second feeder cells may be the same or may be different.

In certain embodiments, in step (3), the culturing is carried out in the G-Rex® 10M System.

In certain embodiments, in step (3), the culturing is carried out in CliniMACS Prodigy®.

In certain embodiments, the cells are cryopreserved after the first expansion (e.g., after step (3)).

In certain embodiments, the number of TIL cells inoculated for the second expansion (e.g., step (4)) is greater than $20 \times 10^6$.

In certain embodiments, the second culture medium is a liquid culture medium.

In certain embodiments, the second culture medium is a complete culture medium.

In certain embodiments, the complete culture medium comprises a basal culture medium, serum or a serum substitute, L-glutamine and/or a cytokine.

In certain embodiments, the basal culture medium comprises but is not limited to: AIM-V, RPMI-1640, optimizer CTS T cell expansion basal culture medium, X-vivo 15, TexMACS, or combinations thereof.

In certain embodiments, the serum or the serum substitute comprises but is not limited to: Human AB Serum or CTS™ Immune Cell Serum Replacement (SR).

In certain embodiments, L-glutamine comprises but is not limited to:

L-glutamine 100× or SG-200 Stable L-Glutamine Dipeptide.

In certain embodiments, the cytokine comprises but is not limited to: IL2, IL7, IL-15, IL-21, or combinations thereof.

In certain embodiments, a concentration range of IL2 is about 300 IU/ml to about 10000 IU/ml.

In certain embodiments, a concentration range of IL7, IL15 and/or IL21 is about 10 ng/ml to about 100 µg/ml.

In certain embodiments, the second culture medium further contains a component including OKT3, anti-CD3 Dynabeads®, anti-CD3/anti-CD28 Dynabeads®, or combinations thereof.

In certain embodiments, in the second culture medium, OKT3 has a concentration of about 10 ng/ml to about 100 µg/ml.

In certain embodiments, in the second culture medium, the quantity (number) of the anti-CD3 Dynabeads® is about 1-3 times the number of TIL cells inoculated. In certain embodiments, in the second culture medium, the quantity (number) of the anti-CD3/anti-CD28 Dynabeads® is 1-3 times the number of TIL cells inoculated.

In certain embodiments, in step (4), the culturing is carried out in a culture container such as Prodigy®, WAVE or G-Rex® (Wilson Wolf Manufacturing).

In certain embodiments, the first expanded cell population and the second feeder cells are inoculated in a Xuri W25 cellbag.

In certain embodiments, the volume of the cell bag is about 2 L to about 50 L. In certain embodiments, the Xuri W25 comprises one or more parameters selected from the following:

| Parameter | Setting range |
|---|---|
| Rocking speed | 2-20 rpm |
| Rocking angle | 2-12° |
| $CO_2$ ratio | 3-8% |
| $O_2$ ratio | 15%-50% |
| Temperature | 25-37° C. |
| Gas flow | 0.05-0.5 L/min |

In certain embodiments, when the TIL is expanded in Xuri W25, the culture volume is in a range of about 300 ml to about 25000 ml.

In certain embodiments, when the TIL is expanded in Xuri W25, a density range of the TIL cell is about $0.01 \times 10^6$ cells/ml to about $50 \times 10^6$ cells/ml.

In certain embodiments, when the TIL is expanded in Xuri W25, a perfusion procedure during the culturing process is as follows:

| Cell density | Perfusion rate |
| --- | --- |
| Cell density < 1 × 10⁶/ml | Without perfusion |
| 1 × 10⁶/ml ≤ Cell density < 5 × 10⁶/ml | Perfusion 20% V/Day-40% V/Day |
| 5 × 10⁶/ml ≤ Cell density < 10 × 10⁶/ml | Perfusion 40% V/Day-60% V/Day |
| 10 × 10⁶/ml ≤ Cell density < 15 × 10⁶/ml | Perfusion 60% V/Day-80% V/Day |
| 15 × 10⁶/ml ≤ Cell density < 50 × 10⁶/ml | Perfusion 80% V/Day-200% V/Day |

Note: V is the volume of the culture system.

In certain embodiments, the method further comprises step (5): carrying out re-expansion of the first expanded TIL cell population to obtain TIL cells. In step (5), the re-expansion may be carried out in a culture system such as Prodigy®, WAVE or G-Rex®.

In certain embodiments, in step (5), after re-expansion, washing, concentrating, and/or harvesting of the cells are carried out. The washing and concentrating may be carried out in LOVO/Sefia/Sepax C-Pro/Sepax 2/CS5+/CSE or the like. In some embodiments, the harvesting is performed using a LOVO cell processing system.

In certain embodiments, the parameters of LOVO/Sefia/Sepax C-Pro/Sepax 2/CS5+/CSE (comprising washing and concentrating parameters) are as follows:

the volume of the sample that can be treated is a range of about 50 ml to about 22000 ml;

the rate of the sample flowing into the container ranges from about 50 ml/min to about 200 ml/min;

the rate of the sample flowing out of the container ranges from about 50 ml/min to about 200 ml/min;

the number of washing cycles ranges from about 1 to about 5; and/or after the cells are washed and concentrated, the output volume is a range of about 50 ml to about 2000 ml.

In certain embodiments, a washing solution for washing is selected from a group consisting of 0.9% sodium chloride solution, compound electrolyte (injection) composition, glucose and sodium chloride (injection) composition, or combinations thereof.

In certain embodiments, the washing solution further contains about 0.1% to about 5% of human serum albumin.

In certain embodiments, in step (4), aliquoting is carried out after re-expansion.

In certain embodiments, the aliquoting is carried out by using Cell Connect aliquoting pipelines and Sepax 2, Sepax C-pro or Sefia aliquoting equipment.

In certain embodiments, the aliquoting is carried out after washing and concentrating.

In certain embodiments, the washing and concentrating parameters comprise:

the volume of the sample that can be treated is a range of about 5 ml to about 500 ml;

the output volume of aliquoting is in the range of about 5 ml to about 400 ml; and/or the concentration of DMSO in the cell sample after adding the cryopreservation solution is in the range of 0% to about 10%.

In some embodiments, the method further comprises the step of cryopreserving the cells after the first expansion and/or after the second expansion using a cryopreservation process.

In some embodiments, the cryopreservation process is performed using a 1:1 ratio of harvested TIL population to cryopreservation media.

In some embodiments, the cryopreservation media comprises dimethlysulfoxide (DMSO). In some embodiments, the cryopreservation media comprises 7% to 10% dimethlysulfoxide (DMSO).

In some embodiments, the therapeutic population of TILs harvested after the second expansion comprises sufficient TILs for a therapeutically effective dosage of the TILs.

In some embodiments, the number of TILs sufficient for a therapeutically effective dosage is at least or about $1 \times 10^{10}$, at least or about $2 \times 10^{10}$, at least or about $3 \times 10^{10}$, at least or about $4 \times 10^{10}$, at least or about $5 \times 10^{10}$, at least or about $6 \times 10^{10}$, at least or about $7 \times 10^{10}$, at least or about $8 \times 10^{10}$, at least or about $9 \times 10^{10}$, or at least or about $10 \times 10^{10}$.

A second aspect of the present disclosure provides TIL cells prepared/expanded by the method described in the first aspect of the present disclosure.

A third aspect of the present disclosure provides an application of the TIL cells prepared by the present method in the preparation of anti-tumor drugs.

It should be understood that within the scope of the present disclosure, the above-mentioned technical features of the present disclosure and the technical features specifically described in the following (such as the embodiments) can be combined with each other, so as to form new or preferred technical solutions. Due to space limitations, they will not be repeated one by one here.

DETAILED DESCRIPTION

Figure 1:
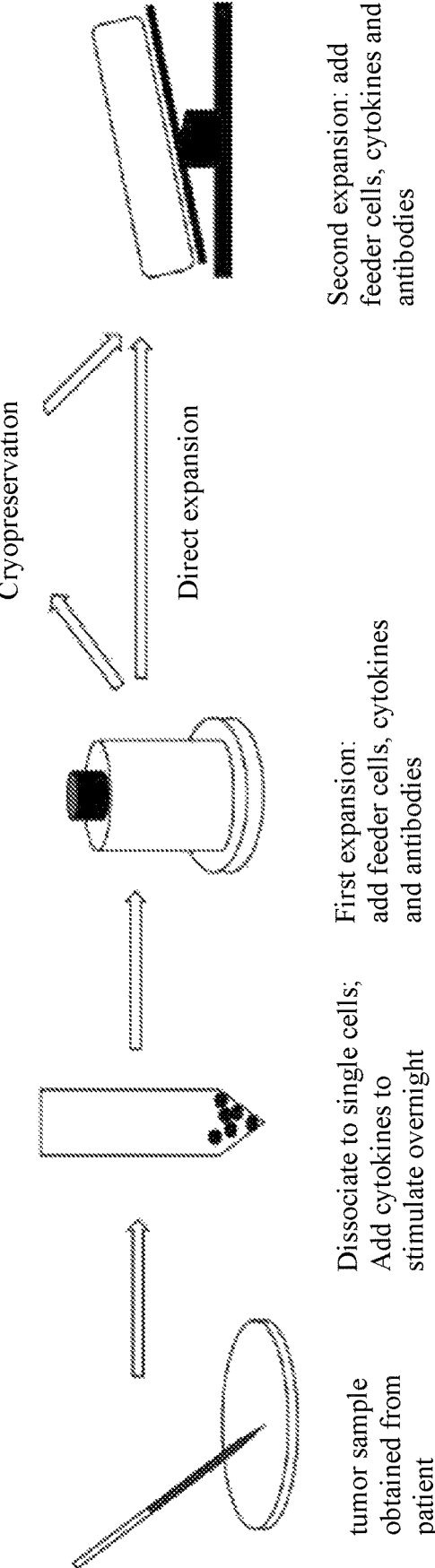
FIG. 1 is a schematic diagram of TIL expansion from a small sample.

The present disclosure provides improved methods for expanding TILs. The methods lead to improved efficacy, improved phenotype, and increased metabolic health of the TILs.

The present disclosure provides for methods that can quickly obtain a large number of TILs from a very small tumor sample. For example, a large number of TIL cells can be produced from a small tumor tissue after dissociation and expansions. The method may involve the use of Prodigy®/G-Rex®/Wave and other cell expansion systems, as well as LOVO/Sefia/Sepax C-Pro/Sepax 2/CS5+/CSE and other closed systems, to carry out TIL washing and packaging, which may improve the production capacity and is suitable for industrial production.

In the present method, the tumor-reactive T cells (e.g., TILs) may be isolated and the cells are culture-expanded to a desired quantity for administration to a patient in need thereof (e.g., in an adoptive cell transfer therapy).

Examples of various cancers to be treated by the present TILs or compositions include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

The present disclosure provides compositions and methods for isolating and culturing tumor-reactive T-cells. In one embodiment, the disclosure provides compositions and methods to isolate and culture tumor infiltrating lymphocytes (TILs).

The disclosure includes compositions and methods for rapidly isolating and culturing cells for use in adoptive immunotherapy. In one embodiment, the isolated cells of are tumor infiltrating lymphocytes (TILs).

The TILs may be isolated and cultured from a sample of solid tumor tissue.

In another aspect, the disclosure includes enriching and expanding TILs for use in a cellular therapy for adoptive transfer. In one embodiment, the TILs are selectively isolated from a tumor sample before in vitro expansion.

In yet another aspect, the cells are cultured in the presence of IL-2.

In still another aspect, the disclosure includes a method of treating a tumor in a patient comprising administering to a patient in need thereof an effective amount of a population of TILs.

Cryopreservation medium may refer to any medium that can be used for cryopreservation of cells. Such media can include media comprising 7% to 10% DMSO. Exemplary media include CryoStor CS10, Hyperthermasol, as well as combinations thereof. The term "CS10" refers to a cryopreservation medium which is obtained from Stemcell Technologies or from Biolife Solutions. The CS10 medium may be referred to by the trade name "CryoStor® CS10". The CS10 medium is a serum-free, animal component-free medium which comprises DMSO.

In general, TILs may be initially obtained from a patient tumor sample ("primary TILs") and then expanded into a larger population for further manipulation as described herein, optionally cryopreserved, thawed or restimulated and optionally evaluated for phenotype and metabolic parameters as an indication of TIL health.

A patient tumor sample may be obtained using methods known in the art, such as via surgical resection, needle biopsy or other means for obtaining a sample that contains a mixture of tumor and TIL cells. In general, the tumor sample may be from any solid tumor, including primary tumors, invasive tumors or metastatic tumors. The tumor sample may also be a liquid tumor, such as a tumor obtained from a hematological malignancy. The solid tumor may be of any cancer type, including, but not limited to, breast, pancreatic, prostate, colorectal, lung, brain, renal, stomach, and skin cancer (including but not limited to squamous cell carcinoma, basal cell carcinoma, and melanoma).

Once obtained, the tumor sample may be fragmented using sharp dissection into small pieces. The TILs may be cultured from these fragments using enzymatic tumor digests. Such tumor digests may be produced by incubation in enzymatic media (e.g., Roswell Park Memorial Institute (RPMI) 1640 buffer, 2 mM glutamate, 10 mcg/mL gentamicine, 30 units/mL of DNase and 1.0 mg/mL of collagenase) followed by mechanical dissociation (e.g., using a tissue dissociator). Tumor digests may be produced by placing the tumor in enzymatic media and mechanically dissociating the tumor for approximately 1 minute, followed by incubation for 30 minutes at 37° C. in 5% $CO_2$, followed by repeated cycles of mechanical dissociation and incubation under the foregoing conditions until only small tissue pieces are present. At the end of this process, if the cell suspension contains a large number of red blood cells or dead cells, a density gradient separation using FICOLL branched hydrophilic polysaccharide may be performed to remove these cells. Alternative methods known in the art may be used, such as those described in U.S. Patent Publication No. 2012/0244133, the disclosure of which is incorporated by reference herein. Any of the foregoing methods may be used in any of the embodiments described herein for methods of expanding TILs or methods treating a cancer.

In some embodiments, fragmentation includes physical fragmentation, including for example, dissection as well as digestion. In some embodiments, the fragmentation is physical fragmentation. In some embodiments, the fragmentation is dissection. In some embodiments, the fragmentation is by digestion. In some embodiments, TILs can be initially cultured from enzymatic tumor digests and tumor fragments obtained from patients. In an embodiment, TILs can be initially cultured from enzymatic tumor digests and tumor fragments obtained from patients.

In some embodiments, the TILs are obtained from tumor digests. In some embodiments, tumor digests are generated by incubation in enzyme media, for example but not limited to, RPMI 1640, 2 mM GlutaMAX, 10 mg/mL gentamicin, 30 U/mL DNase, and 1.0 mg/mL collagenase, followed by mechanical dissociation (GentleMACS, Miltenyi Biotec, Auburn, Calif.). After placing the tumor in enzyme media, the tumor can be mechanically dissociated for approximately 1 minute. The solution can then be incubated for 30 minutes at 37° C. in 5% $CO_2$ and is then mechanically disrupted again for approximately 1 minute. After being incubated again for 30 minutes at 37° C. in 5% $CO_2$, the tumor can be mechanically disrupted a third time for approximately 1 minute. In some embodiments, after the third mechanical disruption if large pieces of tissue were present, 1 or 2 additional mechanical dissociations were applied to the sample, with or without 30 additional minutes of incubation at 37° C. in 5% $CO_2$. In some embodiments, at the end of the final incubation if the cell suspension contains a large number of red blood cells or dead cells, a density gradient separation using Ficoll can be performed to remove these cells.

In some embodiments, the first expansion can proceed for about 7 days to about 16 days, about 9 days to about 14 days, about 5 days to about 16 days, about 6 days to about 16 days, about 8 days to about 16 days, about 9 days to about 16 days, about 10 days to about 16 days, about 11 days to about 16 days, about 12 days to about 16 days, about 9 days to about 12 days, about 8 days to about 12 days, or about 7 days to about 12 days.

In some embodiments, the first TIL expansion can proceed for about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, or about 20 days. In some embodiments, the first TIL expansion can proceed for about 1 day to about 14 days. In some embodiments, the first TIL expansion can proceed for about 2 days to about 14 days. In some embodiments, the first TIL expansion can proceed for about 3 days to about 14 days. In some embodiments, the first TIL expansion can proceed for about 4 days to about 14 days. In some embodiments, the first TIL expansion can proceed for about 5 days to about 14 days. In some embodiments, the first TIL expansion can proceed for about 6 days to about 14 days. In some embodiments, the first TIL expansion can proceed for about 7 days to about 14 days. In some embodiments, the first TIL expansion can proceed for about 8 days to about 14 days. In some embodiments, the first TIL expansion can proceed for about 9 days to about 14 days. In some embodiments, the first TIL expansion can proceed for about 10 days to about 14 days. In some embodiments, the first TIL expansion can proceed for about 11 days to about 14 days. In some embodiments, the first TIL expansion can proceed for about 12 days to about 14 days. In some embodiments, the first TIL expansion can proceed for about 13 days to about 14 days. In some embodiments, the first TIL expansion can proceed for about 1 day to about 11 days. In some embodiments, the first TIL expansion can proceed for about 2 days to about 11 days. In some embodiments, the first TIL expansion can proceed for about 3 days to about 11 days. In some embodiments, the first TIL expansion can proceed for about 4 days to about 11 days. In some embodiments, the first TIL expansion can proceed for about 5 days to about 11 days. In some embodiments, the first TIL expansion can proceed for about 6 days to about 11 days. In some embodiments, the first TIL expansion can proceed for about 7 days to about 11 days. In some embodiments, the first TIL expansion can proceed for about 8 days to about 11 days. In some embodiments, the first TIL expansion can proceed for about 9 days to about 11 days. In some embodiments, the first TIL expansion can proceed for about 10 days to about 11 days.

In some embodiments, the second expansion can proceed for about 7 days to about 16 days, about 9 days to about 14 days, about 5 days to about 16 days, about 6 days to about 16 days, about 8 days to about 16 days, about 9 days to about 16 days, about 10 days to about 16 days, about 11 days to about 16 days, about 12 days to about 16 days, about 9 days to about 12 days, about 8 days to about 12 days, about 7 days to about 12 days, about 5 days to about 18 days, about 6 days to about 18 days, about 7 days to about 18 days, about 8 days to about 18 days, about 9 days to about 18 days, about 10 days to about 18 days, about 11 days to about 18 days, about 12 days to about 18 days, about 13 days to about 18 days, about 5 days to about 16 days, about 6 days to about 16 days, about 8 days to about 16 days, about 9 days to about 16 days, about 10 days to about 16 days, about 11 days to about 16 days, about 12 days to about 16 days, In some embodiments, the second TIL expansion can proceed for about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, or about 20 days. In some embodiments, the second TIL expansion can proceed for about 1 day to about 14 days. In some embodiments, the second TIL expansion can proceed for about 2 days to about 14 days. In some embodiments, the second TIL expansion can proceed for about 3 days to about 14 days. In some embodiments, the second TIL expansion can proceed for about 4 days to about 14 days. In some embodiments, the second TIL expansion can proceed for about 5 days to about 14 days. In some embodiments, the second TIL expansion can proceed for about 6 days to about 14 days. In some embodiments, the second TIL expansion can proceed for about 7 days to about 14 days. In some embodiments, the second TIL expansion can proceed for about 8 days to about 14 days. In some embodiments, the second TIL expansion can proceed for about 9 days to about 14 days. In some embodiments, the second TIL expansion can proceed for about 10 days to about 14 days. In some embodiments, the second TIL expansion can proceed for about 11 days to about 14 days. In some embodiments, the second TIL expansion can proceed for about 12 days to about 14 days. In some embodiments, the second TIL expansion can proceed for about 13 days to about 14 days. In some embodiments, the second TIL expansion can proceed for about 1 day to about 11 days. In some embodiments, the second TIL expansion can proceed for about 2 days to about 11 days. In some embodiments, the second TIL expansion can proceed for about 3 days to about 11 days. In some embodiments, the second TIL expansion can proceed for about 4 days to about 11 days. In some embodiments, the second TIL expansion can proceed for about 5 days to about 11 days. In some embodiments, the second TIL expansion can proceed for about 6 days to about 11 days. In some embodiments, the second TIL expansion can proceed for about 7 days to about 11 days. In some embodiments, the second TIL expansion can proceed for about 8 days to about 11 days. In some embodiments, the second TIL expansion can proceed for about 9 days to about 11 days. In some embodiments, the second TIL expansion can proceed for about 10 days to about 11 days.

In certain embodiments, in the first culture medium (for the first expansion), OKT3 may have a concentration ranging from about 3 ng/ml to about 100 ng/ml, about 1 ng/ml to about 100 ng/ml, about 5 ng/ml to about 100 ng/ml, about 10 ng/ml to about 100 ng/ml, about 15 ng/ml to about 100 ng/ml, about 20 ng/ml to about 100 ng/ml, about 30 ng/ml to about 100 ng/ml, about 40 ng/ml to about 100 ng/ml, about 50 ng/ml to about 100 ng/ml, about 60 ng/ml to about 100 ng/ml, about 3 ng/ml to about 80 ng/ml, about 3 ng/ml to about 60 ng/ml, about 3 ng/ml to about 50 ng/ml, about 5 ng/ml to about 50 ng/ml, about 10 ng/ml to about 50 ng/ml, or about 3 ng/ml to about 30 ng/ml. In some embodiments, the cell culture medium comprises about 30 ng/mL of OKT3 antibody. In an embodiment, the cell culture medium comprises about 0.1 ng/mL, about 0.5 ng/mL, about 1 ng/mL, about 2.5 ng/mL, about 5 ng/mL, about 7.5 ng/mL, about 10 ng/mL, about 15 ng/mL, about 20 ng/mL, about 25 ng/mL, about 30 ng/mL, about 35 ng/mL, about 40 ng/mL, about 50 ng/mL, about 60 ng/mL, about 70 ng/mL, about 80 ng/mL, about 90 ng/mL, about 100 ng/mL, about 200 ng/mL, about 500 ng/mL, and about 1 pg/mL of OKT3 antibody. In an embodiment, the cell culture medium comprises between 0.1 ng/mL and 1 ng/mL, between 1 ng/mL and 5 ng/mL, between 5 ng/mL and 10 ng/mL, between 10 ng/mL and 20 ng/mL, between 20 ng/mL and 30 ng/mL, between 30 ng/mL and 40 ng/mL, between 40 ng/mL and 50 ng/mL, and between 50 ng/mL and 100 ng/mL of OKT3 antibody.

In certain embodiments, in the second culture medium (for the second expansion), OKT3 may have a concentration of about 10 ng/ml to about 100 μg/ml, about 1 ng/ml to about 100 μg/ml, about 20 ng/ml to about 100 μg/ml, about 50 ng/ml to about 100 μg/ml, about 100 ng/ml to about 100 μg/ml, about 500 ng/ml to about 100 μg/ml, about 1 μg/ml to about 100 μg/ml, about 10 μg/ml to about 100 μg/ml, about 50 μg/ml to about 100 μg/ml, about 10 ng/ml to about 50 μg/ml, about 50 ng/ml to about 50 μg/ml, about 100 ng/ml to about 50 μg/ml, about 500 ng/ml to about 50 μg/ml, about 1 μg/ml to about 50 μg/ml, about 10 μg/ml to about 50 μg/ml, about 50 ng/ml to about 10 μg/ml, about 100 ng/ml to about 10 μg/ml, about 200 ng/ml to about 10 μg/ml, about 500 ng/ml to about 10 μg/ml, about 1 μg/ml to about 10 μg/ml, about 10 ng/ml to about 1 μg/ml, about 100 ng/ml to about 1 μg/ml, about 200 ng/ml to about 1 μg/ml, about 500 ng/ml to about 1 μg/ml, or about 3 ng/ml to about 30 ng/ml. In some embodiments, the cell culture medium comprises about 30 ng/mL of OKT3 antibody. In an embodiment, the cell culture medium comprises about 0.1 ng/mL, about 0.5 ng/mL, about 1 ng/mL, about 2.5 ng/mL, about 5 ng/mL, about 7.5 ng/mL, about 10 ng/mL, about 15 ng/mL, about 20 ng/mL, about 25 ng/mL, about 30 ng/mL, about 35 ng/mL, about 40 ng/mL, about 50 ng/mL, about 60 ng/mL, about 70 ng/mL, about 80 ng/mL, about 90 ng/mL, about 100 ng/mL, about 200 ng/mL, about 500 ng/mL, and about 1 pg/mL of OKT3 antibody. In an embodiment, the cell culture medium comprises between 0.1 ng/mL and 1 ng/mL, between 1 ng/mL and 5 ng/mL, between 5 ng/mL and 10 ng/mL, between 10 ng/mL and 20 ng/mL, between 20 ng/mL and 30 ng/mL, between 30 ng/mL and 40 ng/mL, between 40 ng/mL and 50 ng/mL, and between 50 ng/mL and 100 ng/mL of OKT3 antibody.

In some embodiments, the feeder cells are antigen-presenting cells (APCs) such as PBMCs. In an embodiment, the ratio of TILs to feeder cells (e.g., PBMCs and/or antigen-presenting cells) in the first expansion and/or the second expansion is about 1 to 25, about 1 to 50, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500. In an embodiment, the ratio of TILs to the feeder cells (e.g., PBMCs) in the first expansion and/or the second expansion is between 1 to 50 and 1 to 300. In an embodiment, the ratio of TILs to feeder cells (e.g., PBMCs and/or antigen-presenting cells) in the first expansion and/or the second expansion is between 1 to 100 and 1 to 200.

In certain embodiments, the feeder cells are peripheral blood mononuclear cells (PBMCs) obtained from standard whole blood units from healthy blood donors. The PBMCs may be obtained using standard methods such as Ficoll-Paque gradient separation.

The feeder cells (e.g., PBMCs) may be inactivated, e.g., via irradiation or heat treatment, before being used in the first or second expansion.

The immune cells may be tumor-infiltrating lymphocytes (TIL), cytotoxic T lymphocytes (CTL), natural killer (NK) cells, or lymphokine-activated killer (LAK) cells, for example. The methods described herein may be used to treat a number of diseases including cancer, infectious diseases, and immunodeficiencies.

In one embodiment, the TILs are autologous to the patient.

In certain embodiment, tumor-reactive T cells are isolated from solid tumor tissue. The tumor tissue is removed from the patient prior to preparing the TILs. The TILs can further be enriched by culturing the cells in the presence of IL-2.

Another embodiment includes obtaining T cells from tumor tissue. The tumor tissue may include cancerous cells. The T cells may be isolated from the bulk of the tumor tissue prior to culturing or expansion, such as by flow cytometry, negative or positive selection, or other methods.

In another aspect, a population of TILs are isolated from a liquid tumor tissue, such as peripheral blood, bone marrow, or ascites.

The present disclosure also includes a method of obtaining an expanded number of TILs from a subject for adoptive cell immunotherapy comprising obtaining a tumor tissue sample from the subject and isolating TILs from the tumor tissue.

The present invention encompasses methods for the isolation and expansion of a population of tumor-reactive T cells.

The culturing apparatus can be of any culture apparatus commonly used in culturing cells in vitro.

Cell culture medium may be replaced during the culturing of the cells at any time. For example, the cell medium may be replaced every 3 to 4 days.

The cells may be harvested from the culture apparatus at any desired stage whereupon the cells can be used immediately or cryopreserved to be stored for use at a later time.

In one aspect, the disclosure includes a method of culturing tumor-reactive T cells comprising isolating and culturing cells from a sample of solid tumor tissue in a closed-chamber. Culturing the cells in a closed chamber or sealed apparatus may prevent or substantially reduce the risk of contamination. The closed chamber or sealed apparatus may include any appropriate culture vessel used in clinical laboratories for producing cellular therapies.

In one embodiment, the cells can be cultured in the presence of IL2.

In one embodiment, the cells can be cultured in the presence of an immune cell stimulating ligand, such as anti-CD3 antibody (or fragments thereof) and/or anti-CD28 antibody (or fragments thereof).

In another embodiment, the anti-CD3 antibodies (or fragments thereof) and/or anti-CD28 antibodies (or fragments thereof) are bound to beads that are cultured with the cells. The anti-CD3/CD28 antibodies (or fragments thereof) may be immobilized on the beads, either on the same bead, i.e., "cis," or to separate beads, i.e., "trans." In one embodiment, a 1:1 ratio of each antibody (or fragments thereof) bound to the beads for TIL cell expansion and cell growth is used. In one embodiment, the ratio of CD3:CD28 antibody (or fragments thereof) bound to the beads ranges from 100:1 to 1:100 and all integer values there between. In one aspect of the present disclosure, more anti-CD28 antibody (or fragments thereof) is bound to the particles than anti-CD3 antibody (or fragments thereof), i.e., the ratio of CD3:CD28 is less than 1:1. In certain embodiments of the present disclosure, the ratio of anti-CD28 antibody (or fragments thereof) to anti-CD3 antibody (or fragments thereof) bound to the beads is greater than 2:1. In one particular embodiment, an about 1:100 anti-CD3:anti-CD28 ratio of antibody (or fragments thereof) bound to beads is used. In another embodiment, an about 1:75 anti-CD3:anti-CD28 ratio of antibody (or fragments thereof) bound to beads is used. In a further embodiment, an about 1:50 anti-CD3:anti-CD28 ratio of antibody (or fragments thereof) bound to beads is used. In another embodiment, an about 1:30 anti-CD3:anti-CD28 ratio of antibody (or fragments thereof) bound to beads is used. In one preferred embodiment, an about 1:10 anti-CD3:anti-CD28 ratio of antibody (or fragments thereof) bound to beads is used. In another embodiment, an about 1:3 anti-CD3:anti-CD28 ratio of antibody (or fragments thereof) bound to the beads is used. In yet another embodiment, an about 3:1 anti-CD3:anti-CD28 ratio of antibody (or fragments thereof) bound to the beads is used.

In certain embodiments, the microbeads are polymer microbeads. In certain embodiments, the microbeads are magnetic microbeads. In certain embodiments, the microbeads are magnetic polymer microbeads. In certain embodiments, the microbeads are superparamagnetic polymer microbeads. Polymers may include polystyrene, polyesters, polyethers, polyacrylates, polyacrylamides, polyamines, polyethylene imines, polyquarternium polymers, polyphosphazenes, polyvinylalcohols, polyvinylacetates, polyvinylpyrrolidones, block copolymers, or polyurethanes. In certain embodiments, the microbeads are magnetic beads. In certain embodiments, the microbeads are Dynabeads®. In certain embodiments, the microbeads (e.g., Dynabeads®) are monodisperse/homogeneous, superparamagnetic and polymeric microspheres comprising $\gamma Fe_2O_3$ and $Fe_3O_4$ magnetic materials. The microbeads are coated with a layer of polymeric material, which acts as a carrier for adsorbing or binding antibodies specific for CD3 and/or CD28 cell surface molecules.

Conditions appropriate for cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-$\gamma$, IL-4, IL-7, GM-CSF, IL-10, IL-12, IL-15, TGFP, and TNF-$\alpha$ or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, $\alpha$-MEM, F-12, X-Vivo 15, and X-Vivo 20, Optimizer, with added amino acids, sodium pyruvate, 5 and vitamins, either serum-free or supplemented with an appropriate amount of serum (or plasma) or a defined set of hormones, and/or an amount of cytokine(s) sufficient for the growth and expansion of cells. The target cells are maintained under conditions necessary to support growth, for example, an appropriate temperature (e.g., 37° C.) and atmosphere (e.g., air plus 5% $CO_2$).

The present disclosure provides a method for preparing TIL cells. The method may comprise:

(1) providing an initial cell population containing TIL cells from a tumor sample, wherein the number of TIL cells in the initial cell population is n0;

(2) optionally carrying out a pretreatment on the initial cell population, the pretreatment comprising culturing in the presence of IL7, IL15 and/or IL21 cytokines for 6 to 36 hours (preferably 8 to 30 hours, more preferably 10 to 24 hours), to obtain a pretreated initial cell population;

(3) in a first culture container, co-culturing the initial cell population obtained in a previous step and first feeder cells in a first culture medium for a period of time t1 so as to obtain a first expanded cell population containing expanded TIL cells, wherein the number of TIL cells in the first expanded cell population is n1, where n1/n0 is 1000 to 10000, and n1≥1×10$^7$; and (4) transferring the first expanded cell population to a second culture container, and co-culturing with second feeder cells in a second culture medium for a period of time t2 so as to obtain a second expanded cell population containing expanded TIL cells, wherein the number of TIL cells in the second expanded cell population is n2, where n2/n1 is 4000 to 10000, and n2≥1×10$^{10}$.

In certain embodiments, t1 is 7 to 16 days, or 9 to 14 days.

In certain embodiments, t2 is 10 to 16 days, or 12 to 14 days.

In certain embodiments, based on a total number of cells in the second expanded cell population, the purity P of the TIL cells in the second expanded cell population is greater than or equal to 90%.

In certain embodiments, the purity P is at least or about 92%, at least or about 94%, and at least or about P≥95% or higher.

In certain embodiments, a total expansion rate (n1×n2)/n0 of steps (3) and (4) is 0.1×10$^7$ to 20×10$^7$, preferably 1×10$^7$ to 10×10$^7$.

In certain embodiments, the n0 is ≥2000.

In certain embodiments, in step (3), at the beginning of the co-culturing, a cell number ratio R1 of the TIL cells to the first feeder cells in the initial cell population is 1:10 to 1:10000.

In certain embodiments, in step (4), at the beginning of the co-culturing, a cell number ratio R2 of the TIL cells to the second feeder cells in the initial cell population is 1:2 to 1:400.

In certain embodiments, the tumor sample is an in-vitro sample.

In certain embodiments, the tumor sample comprises but is not limited to a solid tumor such as lung cancer, cervical cancer, and ovarian cancer.

Preferably, the tumor sample has a weight of 0.01 to 0.05 g or more, more preferably 0.02 to 0.04 g, such as 0.02 g, 0.03 g or 0.04 g.

Preferably, n0 is 1,000 to 50,000, preferably 2,000 to 50,000, more preferably 2,000 to 10,000, and more preferably 3,000 to 10,000.

In certain embodiments, n1 is 0.1×10$^8$ to 3.0×10$^8$, preferably 0.3×10$^8$ to 2.0×10$^8$.

In certain embodiments, n2 is 1×10$^{10}$ to 2×10$^{11}$.

In certain embodiments, n2 is 1.0×10$^{11}$ to 2.0×10$^{11}$.

In certain embodiments, in the step (1), the tumor sample is dissociated with the dissociation solution to obtain the initial cell population containing TIL cells; and the dissociation solution comprises collagenase II, collagenase IV, DNase, hyaluronidase, and a cell isotonic solution.

In certain embodiments, the isotonic solution comprises but is not limited to a culture medium, DPBS and the like.

In certain embodiments, in the dissociation solution, collagenase II has a concentration of 0.1 g/ml to 10 g/ml; collagenase IV has a concentration of 0.1 g/ml to 10 g/ml; DNase has a concentration of 0.1 g/ml to 10 g/ml; and hyaluronidase has a concentration of 10 U/ml to 1000 U/ml.

In certain embodiments, in step (2), the IL7 cytokine has a concentration of 10 ng/ml to 100 µg/ml.

In certain embodiments, in step (2), the IL15 cytokine has a concentration of 10 ng/ml to 100 µg/ml.

In certain embodiments, in step (2), the IL21 cytokine has a concentration of 10 ng/ml to 100 µg/ml In certain embodiments, in step (3), a cell number ratio of the TIL cells to the first feeder cells in the initial cell population is 1:10 to 1:10000, preferably 1:100 to 1:600, more preferably 1:200 to 1:400.

In certain embodiments, the first culture medium contains a cytokine selected from a group consisting of IL-2, IL-7, IL-15, IL-21, OKT3 antibody, anti-41BB, antiOX40, anti-PD-1, or a combination thereof.

In a further aspect, the present disclosure provides a pharmaceutical composition comprising the TILs.

The TILs can also be used as a pharmaceutical composition in therapy, e.g., cellular therapy, or prevention of diseases. The pharmaceutical composition may be transplanted into an animal or human, for example a human patient. The pharmaceutical composition can be used for the treatment and/or prevention of diseases in mammals, especially humans, possibly including administration of a pharmaceutically effective amount of the pharmaceutical composition to the mammal. Pharmaceutical compositions of the present disclosure may be administered in a manner appropriate to the disease to be treated (or prevented). The quantity and frequency of administration will be determined by such factors as the condition of the patient, and the type and severity of the patient's disease, although appropriate dosages may be determined by clinical trials.

The composition of the TILs, obtained by the present method, may be administered either alone, or as a pharmaceutical composition in combination with diluents and/or with other components such as cytokines or cell populations. Briefly, the present pharmaceutical composition may comprise the TILs, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextran, mannitol; proteins; polypeptides or amino acids such as glycine; antioxidants; chelating agents such as EDTA or glutathione; adjuvants (e.g., aluminum hydroxide); and preservatives.

In an embodiment, TILs expanded using the present methods are administered to a patient as a pharmaceutical composition. In an embodiment, the pharmaceutical composition is a suspension of TILs in a sterile buffer. TILs expanded using the present methods may be administered by any suitable route as known in the art. In some embodiments, the TILs are administered as a single intra-arterial or intravenous infusion, which may last about 30 to 60 minutes. Other suitable routes of administration include intraperitoneal, intrathecal, and intralymphatic.

The TILs provided in the pharmaceutical compositions are effective over a wide dosage range. The exact dosage will depend upon the route of administration, the form in which the composition is administered, the gender and age of the subject to be treated, the body weight of the subject to be treated, and the preference and experience of the attending physician. The clinically established dosages of the TILs may also be used if appropriate. The amounts of the pharmaceutical compositions administered using the methods herein, such as the dosages of TILs, will be dependent on the human or mammal being treated, the severity of the disorder or condition, the rate of administration, the disposition of the active pharmaceutical ingredients and the discretion of the prescribing physician.

In some embodiments, TILs may be administered in a single dose. Such administration may be by injection, e.g., intravenous injection. In some embodiments, TILs may be administered in multiple doses. Dosing may be once, twice, three times, four times, five times, six times, or more than six times per year. Dosing may be once a month, once every two weeks, once a week, or once every other day. Administration of TILs may continue as long as necessary.

An effective amount of the TILs may be administered in either single or multiple doses by any of the accepted modes of administration of agents having similar utilities, including intranasal and transdermal routes, by intra-arterial injection, intravenously, intraperitoneally, parenterally, intramuscularly, subcutaneously, topically, by transplantation, or by inhalation.

The present disclosure also encompasses kits containing the present TILs, or the present composition.

In some embodiments, the kit comprises the present TILs, or the present composition, and instructions for using the kit. Elements may be provided individually or in combinations.

In some embodiments, a kit comprises one or more reagents for use in a process utilizing one or more of the elements described herein. Reagents may be provided in any suitable container. For example, a kit may provide one or more reaction or storage buffers. Reagents may be provided in a form that is usable in a particular assay, or in a form that requires addition of one or more other components before use (e.g., in concentrate or lyophilized form).

The term "tumor infiltrating lymphocyte" or "TIL" refers to white blood cells that have left the bloodstream and migrated into a tumor. TILs may include one or more types of the following cells: CD8+ cytotoxic T cells (lymphocytes), Th1 and Th17 CD4+ T cells, natural killer cells, dendritic cells and M1 macrophages. TIL cell populations can include genetically modified TILs.

TILs can generally be defined either biochemically, using cell surface markers, or functionally, by their ability to infiltrate tumors and effect treatment. TILs may be categorized by expressing one or more of the following biomarkers: CD4, CD8, TCR αβ, CD27, CD28, CD56, CCR7, CD45Ra, CD95, PD-1, and CD25. Additionally and alternatively, TILs can be functionally defined by their ability to infiltrate solid tumors upon reintroduction into a patient.

Tumor-infiltrating lymphocytes (TILs) may refer to mononuclear immune cells that infiltrate tumor tissue or stroma. TILs may include, e.g., T cells, B cells, and NK cells, populations of which can be subcategorized based on function, activity, and/or biomarker expression. For example, a population of TILs may include cytotoxic T cells expressing, e.g., CD3 and/or CD8, and regulatory T cells (also known as suppressor T cells), which are often characterized by FOXP3 expression.

Anti-CD3 antibodies include OKT3, also known as muromonab. Anti-CD3 antibodies also include the UHCT1 clone, also known as T3 and CD3c. Other anti-CD3 antibodies include, for example, otelixizumab, teplizumab, and visilizumab. In certain embodiments, OKT3 may be an anti-human CD3 monoclonal antibody.

As used herein, the term "IL2" is interleukin 2. IL2 includes all forms of IL2 including human and mammalian forms, conservative amino acid substitutions, glycoforms, biosimilars, and variants thereof. IL-2 is described, e.g., in Nelson, J. Immunol. 2004, 172, 3983-88 and Malek, Annu. Rev. Immunol. 2008, 26, 453-79, the disclosures of which are incorporated by reference herein. For example, the term IL-2 encompasses human, recombinant forms of IL-2, such as aldesleukin (PROLEUKIN, available commercially from multiple suppliers in 22 million IU per single use vials), as well as the form of recombinant IL-2 commercially supplied by CellGenix, Inc., Portsmouth, N.H., USA (CELLGRO GMP) or ProSpec-Tany TechnoGene Ltd., East Brunswick, N.J., USA (Cat. No. CYT-209-b) and other commercial equivalents from other vendors. Aldesleukin (des-alanyl-1, serine-125 human IL-2) is a nonglycosylated human recombinant form of IL-2 with a molecular weight of approximately 15 kDa. The term IL-2 also encompasses pegylated forms of IL-2, including the pegylated IL2 prodrug NKTR-214, available from Nektar Therapeutics, South San Francisco, Calif., USA.

The term "antibody" comprises both intact molecules and antibody fragments, such as Fab, Fab', F(ab')2, Fv and single-chain antibodies. The term "antibody" as used herein may refer to polyclonal or monoclonal antibodies. The antibody may be of any species, e.g., murine, rat, sheep, human, etc. For therapeutic purposes, if non-human antigen binding fragments are to be used, these can be humanized by any method known in the art. The antibodies may also be modified antibodies (e.g., oligomers, reduced, oxidized and labeled antibodies).

As used herein, the term "Xuri W25" refers to a Xuri Cell Expansion System W25 (GE Healthcare).

As used herein, the term "complete culture medium" refers to a mixture of a basal culture medium, serum or a serum substitute, L-glutamine and one or more cytokines. The basal culture medium comprises, but is not limited to:

AIM-V, RPMI-1640, an optimizer CTS T cell expansion basal medium, X-vivo 15, and TexMACS. The serum or serum substitute comprises, but is not limited to: Human AB Serum, and CTS immune cell SR. L-glutamine comprises, but is not limited to: L-glutamine 100×, and SG-200 Stable L-Glutamine Dipeptide. Cytokines comprise, but are not limited to: IL-2, IL-7, IL-15 and/or IL-21. In certain embodiments, a concentration range of IL-2 may be about 300 IU/ml to about 6000 IU/ml. A concentration range of IL-7, IL-15 and IL-21 may be about 10 ng/ml to about 100 μg/ml.

The main advantages of the present methods may include the following. From a small tumor tissue or a small number of starting TIL cells, the present methods can produce $10^{11}$ or more TIL cells in a relatively short time period. The method according to the present disclosure can stimulate trace TIL cells in a small tumor sample quickly and easily, so that they can be rapidly expanded with little differentiation. The combination of two rounds of expansion and co-culturing with feeder cells, helps produce a large number of TIL cells in a short time period while suppressing the differentiation of cells towards Teff (effector T cells). In the method according to the present disclosure, the starting numbers of TIL cells, which can be as little as several thousand TIL cells (e.g., ≥2000), are far less than what is required in the prior art. The time used for the entire process can be within about 19 to about 24 days. In the method according to the present disclosure, by adjusting the number of the feeder cells, different starting numbers of TIL cells can be expanded to at least 30 million cells within about 9 to about 14 days. The present methods can generate $1 \times 10^{11}$ to $2 \times 10^{11}$ TIL cells, which is more than what is obtained by the methods in the prior art. In the method according to the present disclosure, the tissue/cells are first dissociated instead of directly being culturing. The method is simpler than those of the prior art, and the desired number of cells can be obtained after two expansions. In the method according to the present disclosure, the cells obtained after the first expansion may be $2.5 \times 10^{7}$, where $10^{11}$ or more TIL cells can be generated after the second expansion. The total expansion ratio far exceeds that of the prior art. In certain embodiments, a combination of IL7/IL15/IL21 is used in the first expansion to increase the ratio of central memory T (Tcm) without affecting the number of cells. In the method according to the present disclosure, the concentration of IL2 used in the first step may be as low as about 300 IU/ml to about 10000 IU/ml.

It is to be understood, although not always explicitly stated, that all numerical designations may be preceded by the term "about". Where particular values are described in the application and claims, unless otherwise stated, the term "about" meaning within an acceptable error range for the particular value should be assumed. As used herein, the term "about" refers to a particular value ±10%.

Conditions to be Treated

The TILs and compositions may be administered to a patient to treat cancer, immunodeficiency diseases, and infections.

The TILs and compositions may be administered to a patient to treat a hyperproliferative disorder.

In some embodiments, the hyperproliferative disorder is cancer. In some embodiments, the hyperproliferative disorder is a solid tumor cancer. In some embodiments, the solid tumor cancer may be melanoma, ovarian cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), renal cancer, or renal cell carcinoma. In some embodiments, the hyperproliferative disorder is a hematological malignancy. In some embodiments, the solid tumor cancer may be chronic lymphocytic leukemia, acute lymphoblastic leukemia, diffuse large B cell lymphoma, non-Hodgkin's lymphoma, Hodgkin's lymphoma, follicular lymphoma, or mantle cell lymphoma.

The TILs may be administered to a patient suffering from impairment in immune activity (such as lymphocyte activity, natural killer cell activity, etc.). For instance, the patient may have a hypoxic tumor that is resistant to untreated immune cells. Alternatively, the patient may suffer from an infectious disease such as a viral infection, bacterial infection, fungal infection, or other eukaryotic cell infection (i.e., protozoal). The compositions and cells herein may be used to treat any disease that causes inflammation. The compositions and cells may also be used to treat any disease in which there is need to increase the potency of anti-pathogen T cells.

The present disclosure provides a method of treating a tumor in a patient comprising administering to a patient in need thereof an effective amount of a population of the TILs.

In some embodiments, the cancer includes, but is not limited to, melanoma, ovarian cancer, cervical cancer, non-small-cell lung cancer (NSCLC), lung cancer, bladder cancer, breast cancer, cancer caused by human papilloma virus, colon cancer, esophageal cancer, endometrial cancer, head and neck cancer (including head and neck squamous cell carcinoma (HNSCC)), renal cancer, and renal cell carcinoma.

The TILs may be administered to a patient to treat a hematological malignancy or a solid tumor.

The term "hematological malignancy" refers to mammalian cancers and tumors of the hematopoietic and lymphoid tissues, including but not limited to tissues of the blood, bone marrow, lymph nodes, and lymphatic system. Hematological malignancies are also referred to as "liquid tumors." Hematological malignancies include, but are not limited to, acute lymphoblastic leukemia (ALL), chronic lymphocytic lymphoma (CLL), small lymphocytic lymphoma (SLL), acute myelogenous leukemia (AML), chronic myelogenous leukemia (CML), acute monocytic leukemia (AMoL), Hodgkin's lymphoma, and non-Hodgkin's lymphomas. The term "B cell hematological malignancy" refers to hematological malignancies that affect B cells. Liquid tumor cancers include, but are not limited to, leukemias, myelomas, and lymphomas, as well as other hematological malignancies.

Solid tumors may be benign or malignant. Solid tumors may include malignant, neoplastic, or cancerous solid tumors. Solid tumor cancers include, but are not limited to, sarcomas, carcinomas, and lymphomas, such as cancers of the lung, breast, prostate, colon, rectum, and bladder. In some embodiments, the cancer is selected from cervical cancer, head and neck cancer (including, for example, head and neck squamous cell carcinoma (HNSCC)) glioblastoma, ovarian cancer, sarcoma, pancreatic cancer, bladder cancer, breast cancer, triple negative breast cancer, and non-small cell lung carcinoma.

In certain embodiments, inflammatory diseases include, but are not limited to, asthma, autoimmune diseases (such as multiple sclerosis and rheumatoid arthritis), chronic inflammation, chronic prostatitis, diabetes (including diabetic ulcers) glomerulonephritis, hypersensitivities, inflammatory bowel diseases, pelvic inflammatory disease, reperfusion injury, rheumatoid arthritis, or vasculitis.

When the disease is a viral infection, it may be caused by (for instance) any one of a member of the Adenoviridae family (such as adenovirus), a member of the Coronavirus family (such as SARS), a member of the Picornaviridae family (such as coxsackievirus, hepatitis A virus, or poliovirus), a member of the Herpesviridae family (such as Epstein-Barr virus, herpes simplex, type 1, herpes simplex, type 2, human cytomegalovirus, human herpesvirus, type 8, or varicella-zoster virus), a member of the Hepadnaviridae family (such as hepatitis B virus), a member of the Flaviviridae family (such as hepatitis C virus, yellow fever virus, dengue virus, west Nile virus), a member of the Retroviridae family (such as HIV or HTLV-1), a member of the Orthomyxoviridae family (such as influenza virus), a member of the Paramyxoviridae family (such as measles virus, mumps virus, parainfluenza virus, respiratory syncytial virus), a member of the Papovaviridae family (such as papillomavirus), a member of the Rhabdoviridae family (such as rabies virus), or a member of the Togaviridae family (such as Rubella virus). In certain embodiments, the virus is a ssDNA virus, a dsDNA virus, a ssRNA virus, or a dsRNA virus. The virus may be enveloped or non-enveloped.

In some embodiments, the disease to be treated is cancer, such as breast cancer; bladder cancer; lung cancer; prostate cancer; thyroid cancer; leukemias and lymphomas such as CML (chronic myelocytic leukemia), ALL (acute lymphoblastic leukemia), AML (acute myelocytic leukemia), PML (pro-myelocytic leukemia); colon cancer; glioma; seminoma; liver cancer; pancreatic cancer; bladder cancer; renal cancer; cervical cancer; testicular cancer; head and neck cancer; ovarian cancer; neuroblastoma and melanoma.

It will be appreciated that the treatment methods herein may be employed with any mammal such as human, cat, dog, horse, cow, sheep or pig. In some embodiments, the subject is a vertebrate. In certain embodiments, the subject is a mammal.

In certain embodiments, the cells of the invention can be used in combination with a therapeutic agent including but is not limited to an anti-tumor, an anti-cancer agent, and the like.

In certain embodiments, the anti-tumor or anti-cancer agent is an alkylating drug, a folate antagonist, a purine antagonist, a pyrimidine antagonist, a spindle poison, a podophyllotoxin, an antibiotic, a nitrosourea, an inorganic ion, a biologic response modifier, an enzyme, or a hormone.

In certain embodiments, the adoptive immunotherapy is combined with a second treatment that augments the immune response. The second treatment may be, for example, an adjuvant and/or a cytokine. Examples of cytokines include, but are not limited to, lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); epidermal growth factor; hepatic growth factor; fibroblast growth factor; prolactin; placental lactogen; tumor necrosis factor-α and tumor necrosis factor-β; mullerian-inhibiting substance; mouse gonadotropin-associated peptide; inhibin; activin; vascular endothelial growth factor; integrin; thrombopoietin (TPO); nerve growth factors such as NGF-α; platelet-growth factor; transforming growth factors (TGFs) such as TGF-α and TGF-β; insulin-like growth factor-I and —II; erythropoietin (EPO); osteoinductive factors; interferons such as interferon-α, -β and -γ colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-10, IL-11, IL-12; a tumor necrosis factor such as TNF-α or TNF-β; and other polypeptide factors including LIF and kit ligand (KL). Cytokines include proteins from natural sources or from recombinant cell culture and biologically active equivalents of the native sequence cytokines.

The present disclosure will be further explained below in conjunction with specific embodiments. It should be understood that these embodiments are only used to illustrate the present disclosure and not to limit the scope of the present disclosure. The experimental methods that do not indicate specific conditions in the following examples usually follow the conventional conditions or the conditions recommended by the manufacturers. Unless otherwise stated, the percentages and parts are calculated by weight.

Example 1

Figure 2:
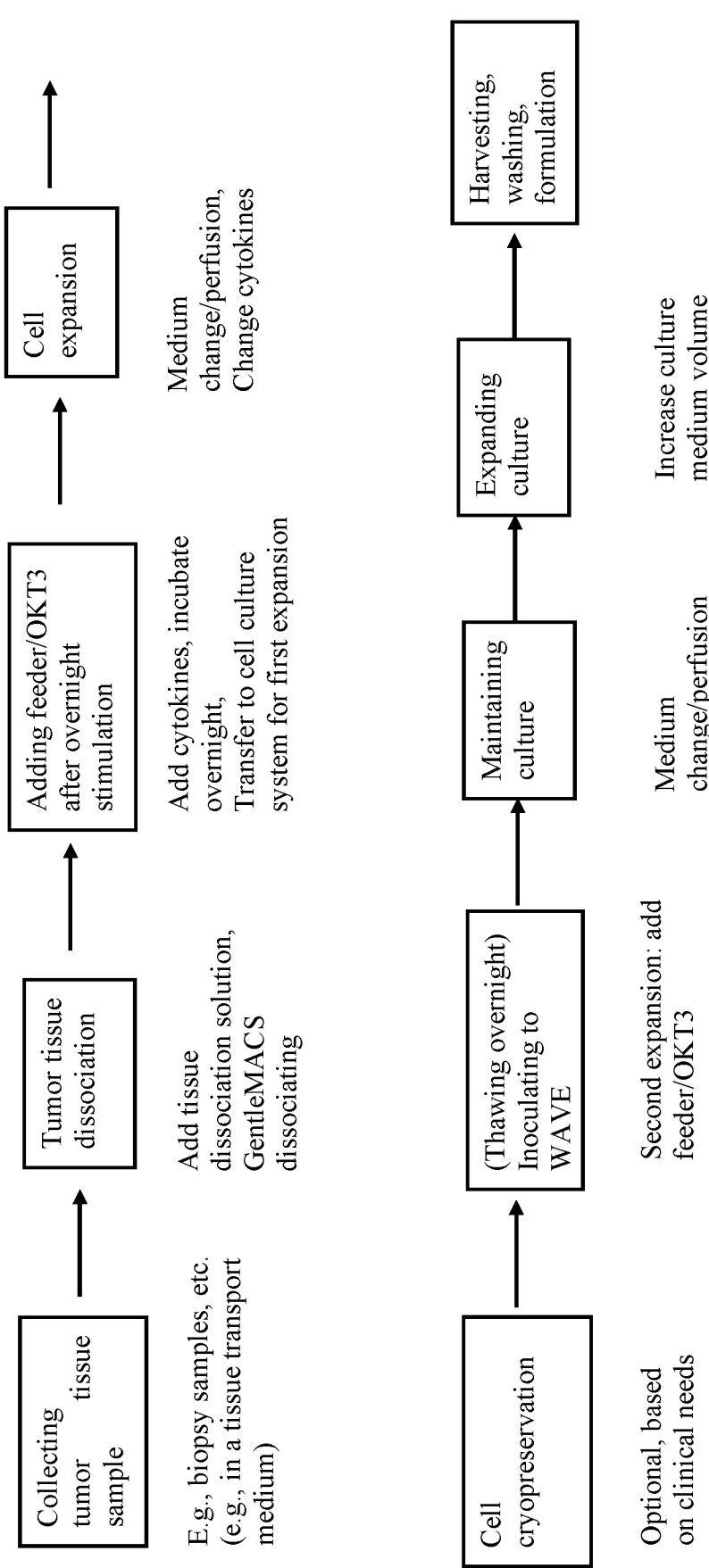
FIG. 2 is a process flow diagram of TIL expansion from a small sample.

Methods for preparing TIL cells were studied. A schematic diagram of the expansion of TILs in a small tumor sample is shown in FIG. 1, and a process flow chart is shown in FIG. 2. The method is as follows:

1. Tumor Tissue Dissociation:

a. Tumor tissue was weighed, rinsed with DPBS several times, and transferred to a cell culture dish. After the tumor tissue was cut into small pieces with a disposable scalpel, a dissociation solution was added at the ratio of about 5 to 50 ml/g (dissociation solution volume/sample weight). The small tumor tissue pieces in the dissociation solution were put into one or more reaction containers, such as GentleMACS C-tubes or ordinary tubes, transfer bags, cell culture dishes, etc.

The dissociation solution contained collagenase II, collagenase IV, DNase, hyaluronidase, in an isotonic solution. The isotonic solution can comprise, but is not limited to, a culture medium, DPBS, and the like. A concentration range of collagenase II was: 0.1 g/ml to 10 g/ml; a concentration range of collagenase IV was: 0.1 g/ml to 10 g/ml; a concentration range of DNase was: 0.1 g/ml to 10 g/ml; and a concentration range of hyaluronidase was: 10 U/ml to 1000 U/ml.

b. A program was set and run. Different programs were used according to different tumor types of the tumor samples. After the dissociation procedure was over, a C-tube tube was removed from a tissue processor and placed in a centrifuge for centrifugation, so that all tissue dissociated fragments and cells were separated from the suspension.

For different tumor tissues, GentleMACS can use 37° C._h_TDK_1 or 37° C._h_TDK_2 or 37° C._h_TDK_3. Alternatively, a 37° C. incubator may be used in combination with manual pipetting, or mixing by shaking or rotating at 37° C. constant temperature.

c. After the dissociation of the tumor sample, the cell suspension was aspirated, and filtered through a cell strainer (with a strainer pore size of about 20 μm to about 70 μm) to obtain a filtrate containing cells. After centrifugation, the supernatant was removed to obtain dissociated cells (initial cell population).

d. The initial cell population was resuspended in a TIL cell culture medium. IL7, IL15 and IL21 cytokines were added (the IL7, IL15 and IL21 cytokines each had a concentration of about 10 ng/ml to about 100 μg/ml) and cultured for about 6 hours to about 36 hour so as to obtain a pretreated initial cell population.

2. Co-Culture of Feeder Cells and Initial Cell Population (First Expansion)

a. Irradiated feeder cells were re-suspended in the cell culture medium (complete culture medium) in a certain ratio according to the number of TIL cells, and mixed with the above-mentioned pretreated initial cell population. They were then transferred together to G-Rex®10M, when OKT3 antibodies, high-concentration IL2 and other related cytokines and/or antibodies were added.

A cell number ratio of TIL to feeder was in a range of about 1:10 to about 1:10000.

A concentration range of OKT3 was about 3 ng/ml to about 100 ng/ml; and a concentration range of IL2 was about 300 IU/ml to about 10000 IU/ml.

Other related factors comprise, but are not limited to, any combination of IL7/IL15/IL21 and anti-41BB antibody or fragments thereof, anti-OX40 antibody or fragments thereof, anti-PD1 antibody or fragments thereof and other T cell-stimulants.

b. Cell growth and differentiation status were closely monitored. Culture media infusion and replacement were carried out in a timely manner.

During the process, the cells were sampled and counted. After reaching the expected number of cells, the first expansion was started. The expanded cells may be cryopreserved before the second expansion.

The parameters of the first expansion were as follows:

The solution infusion volume range was 2 to 100 ml.

The number of TIL cells harvested after expansion was $2 \times 10^7$ to $2 \times 10^8$.

The first expansion was about 7 days to about 16 days, or about 9 days to about 14 days.

The cryopreservation solution comprises but is not limited to CS10 etc.

Figure 3:
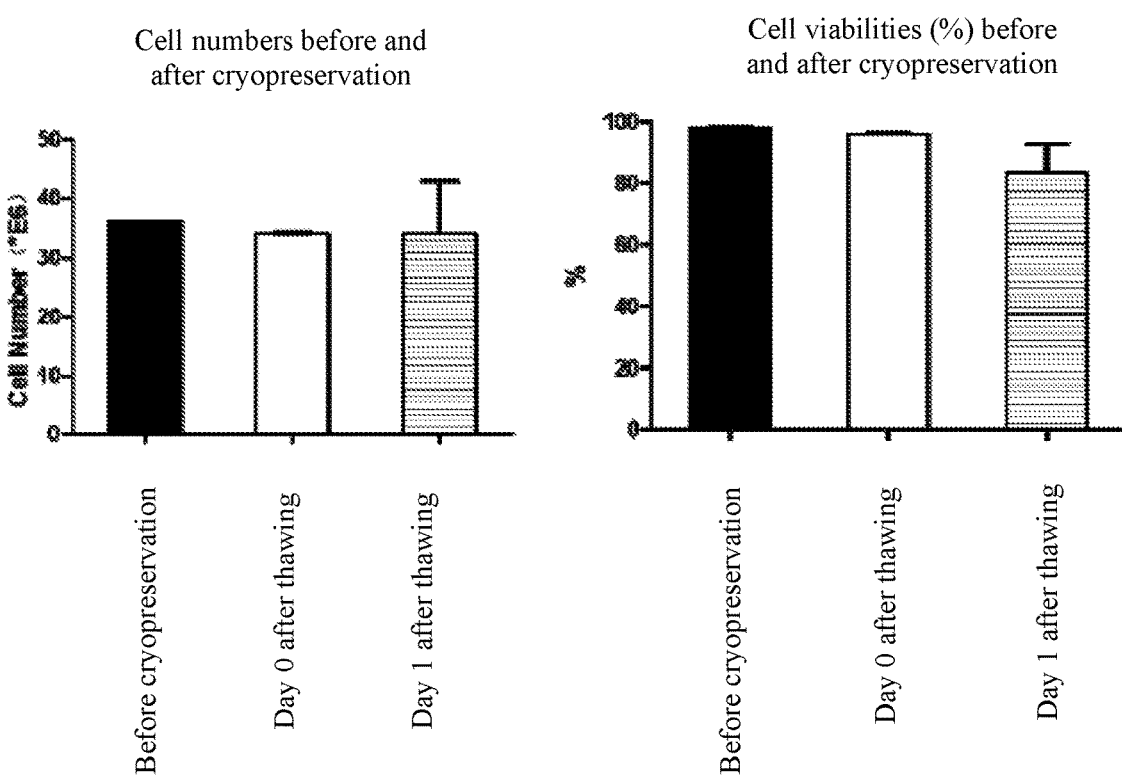
FIG. 3 shows a comparison of the TIL cells obtained from the first expansion before and after cryopreservation.
Figure 3:
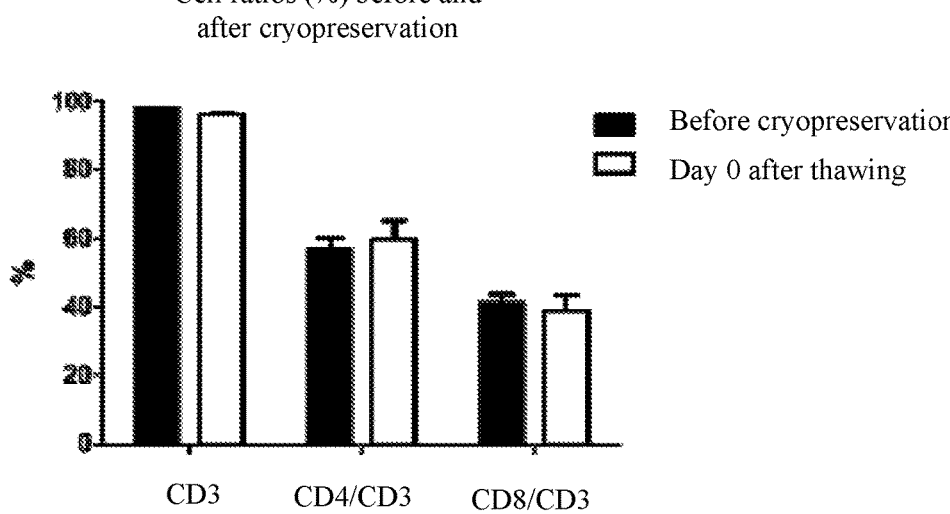

3. Second Co-Culture of Feeder Cells and TIL Cells which are First Expanded Cell Population (Second Expansion)

a. The TIL cells obtained in step 2 (first expanded cell population), or cells that had been cultured for 1 to 3 days after thawing cryopreserved cells, together with the feeder cells, were inoculated into a cell expansion system, such as Prodigy®/Wave/G-Rex® or the like. A comparison of the TIL cells obtained from the first expansion before and after cryopreservation is shown in FIG. 3. Thus, cryopreservation did not significantly affect the properties of the cells. Activating agents OKT3/anti-CD3 Dynabeads/anti-CD3/anti-CD28 Dynabeads were added to rapidly expanding the cells.

After thawing cryopreserved cells, TIL cells were inoculated at a density ranging from about $0.5 \times 10^6$/ml to about $5 \times 10^6$/ml, and were pre-cultured for about 12 hours to about 72 hours.

The cell number ratio of TIL cells to feeder cells was in a range of TIL:Feeder cell=1:20 to 1:400. The number of TIL cells at the time of inoculation was greater than $20 \times 10^6$. A concentration range of activator OKT3 was about 10 ng/ml to about 50 μg/ml. The number of anti-CD3 Dynabeads and anti-CD3/anti-CD28 Dynabeads was 1 to 3 times the number of the inoculated TIL cells.

In the Xuri W25 (2 L/10 L/20 L/50 L Cellbag) example, Xuri W25 equipment parameters are shown in Table 1.

TABLE 1

| Xuri W25 parameters | |
| --- | --- |
| Parameter | Setting range |
| Rocking speed | 2-20 rpm |
| Rocking angle | 2-12° |
| $CO_2$ ratio | 5% |

TABLE 1-continued

| Xuri W25 parameters | |
| --- | --- |
| Parameter | Setting range |
| $O_2$ ratio | 15%-50% |
| Temperature | 37° C. |
| Gas flow | 0.05-0.5 L/min |

When TIL cells were rapidly expanded in Xuri W25 (2 L/10 L/20 L/50 L Cellbag), the culture volume was in a range of about 300 ml to about 25000 ml, and the TIL cell density was in a range of about $0.01 \times 10^6$/ml to about $50 \times 10^6$/ml. The parameters of the perfusion procedure in the culture process are shown in Table 2.

TABLE 2

| Perfusion procedure | |
| --- | --- |
| Cell density | Perfusion rate |
| Cell density $< 1 \times 10^6$/ml | Without Perfusion |
| $1 \times 10^6$/ml ≤ Cell density $< 5 \times 10^6$/ml | Perfusion 20% V/Day-40% V/Day |
| $5 \times 10^6$/ml ≤ Cell density $< 10 \times 10^6$/ml | Perfusion 40% V/Day-60% V/Day |
| $10 \times 10^6$/ml ≤ Cell density $< 15 \times 10^6$/ml | Perfusion 60% V/Day-80% V/Day |
| $15 \times 10^6$/ml ≤ Cell density $< 50 \times 10^6$/ml | Perfusion 80% V/Day-200% V/Day |

Note: V is the volume of the culture system.

The culture medium used was a complete culture medium.

b. After culturing for 6 to 18 days, LOVO/Sefia/Sepax C-Pro/Sepax 2/CS5+/CSE was used for washing and concentrating of the TIL cells after rapid expansion.

Equipment for washing and concentrating of cells comprises but is not limited to LOVO/Sefia/Sepax C-Pro/Sepax 2/CS5+/CSE.

The volume of the sample that was treated was in a range of about 50 ml to about 22000 ml.

The rate of the sample flowing into a container was in a range of about 50 ml/min to about 200 ml/min.

The rate of the sample flowing out of the container was in a range of about 50 ml/min to about 200 ml/min.

The number of washing cycles was in a range of 1 to 5.

After the cells were washed and concentrated, the output volume was in a range of 50 ml to 2000 ml.

The washing solution comprises, but is not limited to, 0.9% sodium chloride solution, compound electrolyte injection composition, and glucose and sodium chloride injection composition, and combinations thereof. The washing solution may also comprise about 0.1% to about 5% (w/v) human serum albumin.

c. Cell Connect aliquoting tubes, Sepax 2, Sepax C-pro, Sefia and other aliquoting equipment or consumables may be used for aliquoting TIL cells after step b.

In step c, a cryopreservation solution was first added, and cells were then aliquoted. An aliquoting system comprises but is not limited to Cell Connect aliquoting tubes, Sepax 2, Sepax C-pro, and Sefia.

The volume of the sample that can be handled was in a range of 5 ml to 500 ml.

The output volume of aliquoting was in the range of 5 ml to 400 ml.

The final concentration of DMSO in the cell sample after adding the cryopreservation solution was in the range of 0% to 10% (v/v).

Experimental Results

Figure 4:
FIG. 4 shows the TIL expansion curves of the first expansion and second expansion.

The TIL expansion curves of the first expansion and the second expansion are shown in FIG. 4. It can be seen from FIG. 4 that both expansions enable TIL cells to be effectively expanded.

Figure 5:
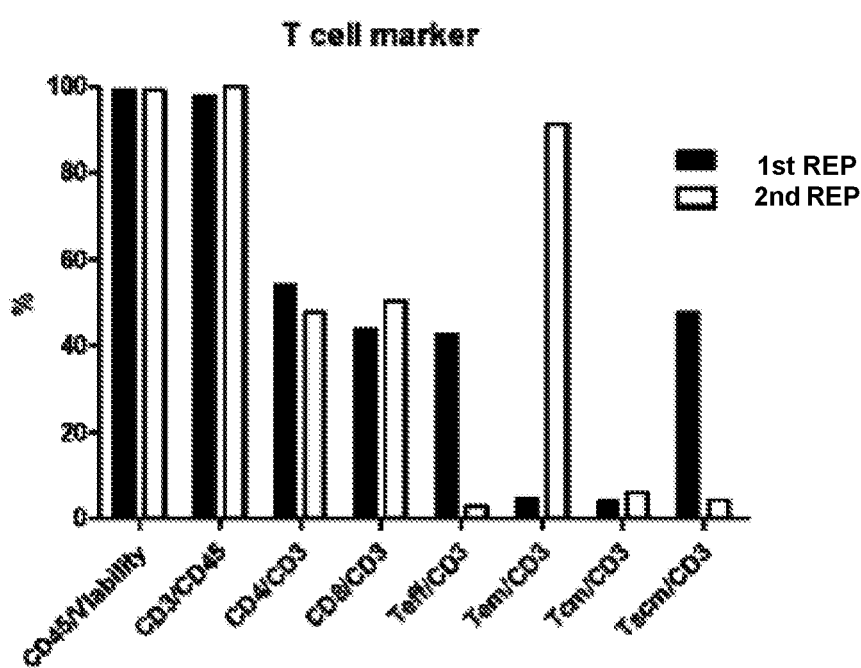
FIG. 5 shows a comparison of the markers of the TIL cells obtained from the first expansion (first rapid expansion protocol (REP) or "1st REP") and second expansion ("2nd REP").
Figure 5:
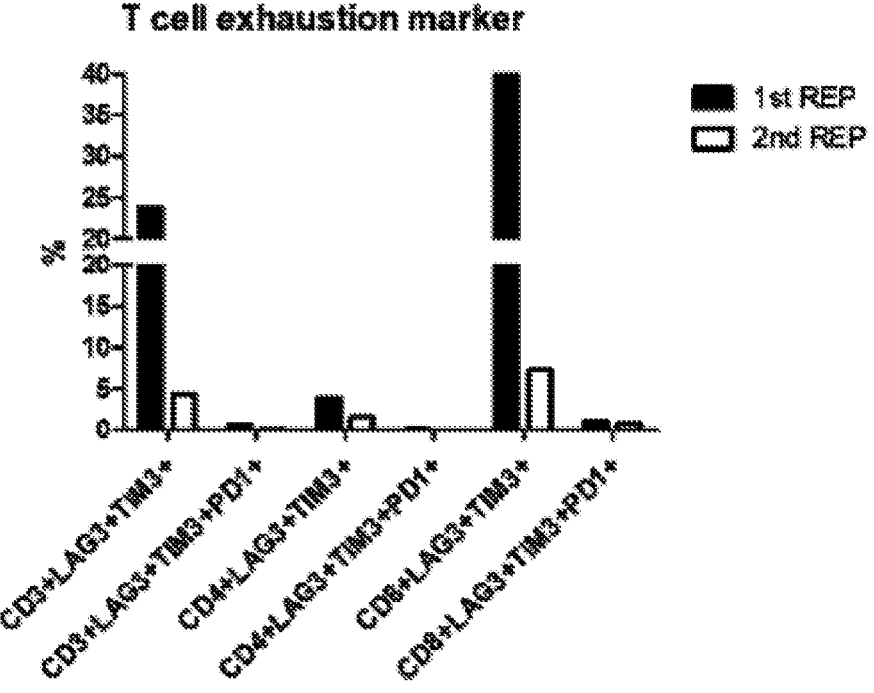

The levels of the cell markers after the first expansion (1st REP) and the second expansion (2nd REP) are shown in FIG. 5. It can be seen from FIG. 5 that the markers of TIL cells were effectively expressed after expansion.

Figure 7:
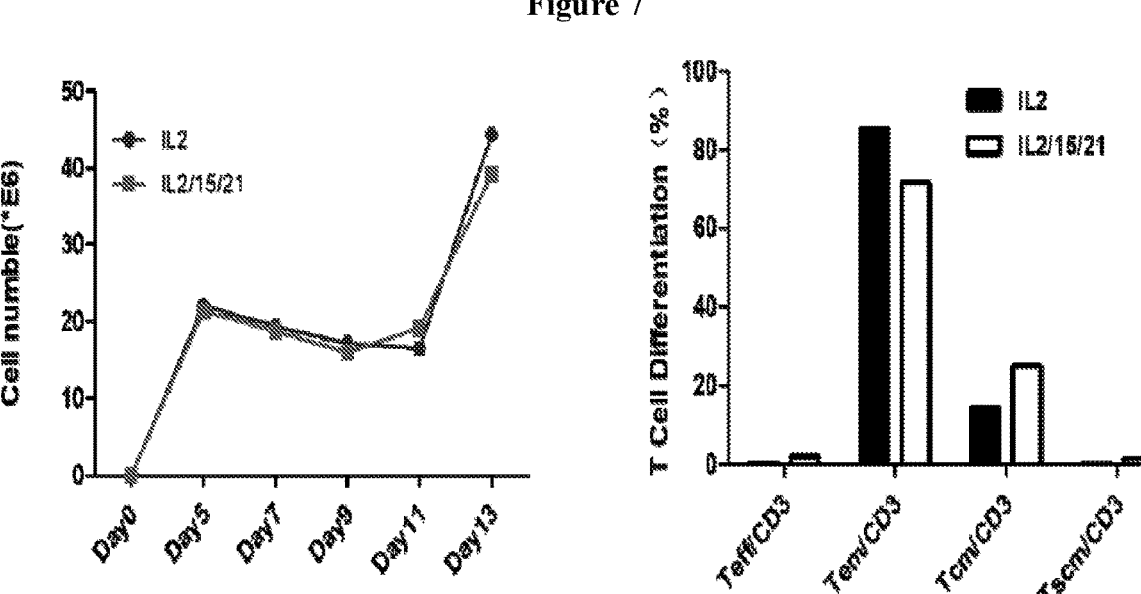
FIG. 7 shows the effects of of added cytokines on the proliferation and differentiation of TIL cells during the first expansion.

In the first expansion, the effects of the added cytokines on the proliferation and differentiation of the TIL cells are shown in FIG. 7. It can be seen from FIG. 7 that the added cytokines can effectively promote the proliferation of TIL cells.

Examples 2-5 and Comparative Examples 1-2

In Examples 2-5, Example 1 was repeated except that tumor samples from different tumor patients were used.

A different pretreatment was used in Comparative Example 1. In Comparative Example 2, OKT3 was not used, and the cultured cells did not directly contact feeder cells.

The differences in the preparation processes between Examples 1-5 and Comparative Examples 1-2 and their expansion effects are shown in Table 3 and Table 4.

TABLE 3

| | Tumor type | Tumor sample weight | Number of starting TILs | Number of TILs after first expansion | Number of TILs after second expansion |
|---|---|---|---|---|---|
| Example 1 | Lung cancer | 0.03 g | 9600 | $1.8 \times 10^8$ | $1.6 \times 10^{11}$ |
| Example 2 | Lung cancer | 0.02 g | 3000 | $1.0 \times 10^8$ | $1.2 \times 10^{11}$ |

TABLE 4

| | Tumor type | Tumor sample weight | Number of starting TILs | Number of TILs after first expansion |
|---|---|---|---|---|
| Example 3 | Lung cancer | 0.04 g | 50000 | $3.5 \times 10^8$ |
| Example 4 | Cervical cancer | NA | 3000 | $8.0 \times 10^7$ |
| Example 5 | Cervical cancer | NA | 200000 | $2.0 \times 10^8$ |
| Comparative Example 1 | Lung cancer | 0.02 g | 2000 | $1.0 \times 10^7$ |
| Comparative Example 2 | Lung cancer | 0.02 g | 5000 | $5.2 \times 10^4$ |

Example 6

Figure 6:
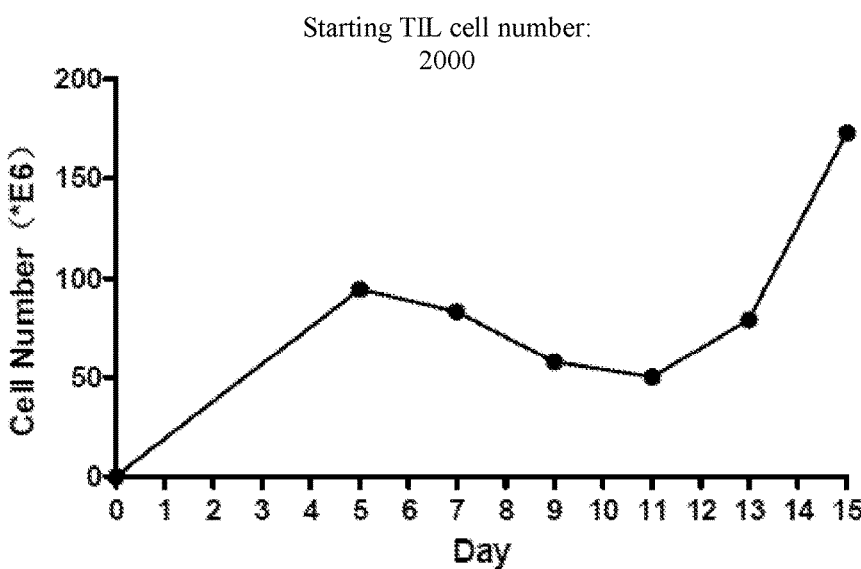
FIG. 6 is a graph showing the growth curve of cells for the first expansion using Prodigy®.

Example 1 was repeated except that the starting number of the cells was 2000 selected TILs after screening. The first expansion was carried out in Prodigy®. The cell growth curve is shown in FIG. 6.

Discussion

A comparison between an embodiment/example of the present method of preparing TIL cells and that of WO2019100023A1 is shown in Table 5.

TABLE 5

| | | Example of the present disclosure | WO2019100023A1-Iovance |
|---|---|---|---|
| Comparison of expanded number | Number of starting TILs | 2.00E+03 | 4.00E+05 |
| | Number of TILs after first expansion | 2.00E+07 | 5.00E+07 |
| | Number of TILs after second expansion | 1.00 to 2.00E+11 | 2.3E+10 to 13.7E+10 |
| | Expansion ratio | 5.0E+7 to 10E+7 | 5.75E+4 to 34.25E+4 |

It can be seen from Table 5 that the method described in the present disclosure can expand a very small number of TIL cells to generate a large number of TIL cells.

The scope of the present disclosure is not limited by what has been specifically shown and described hereinabove. Those skilled in the art will recognize that there are suitable alternatives to the depicted examples of materials, configurations, constructions and dimensions. Numerous references, including patents and various publications, are cited and discussed in the description of this invention. The citation and discussion of such references is provided merely to clarify the description of the present disclosure and is not an admission that any reference is prior art to the invention described herein. All references cited and discussed in this specification are incorporated herein by reference in their entirety. Variations, modifications and other implementations of what is described herein will occur to those of ordinary skill in the art without departing from the spirit and scope of the invention. While certain embodiments of the present disclosure have been shown and described, it will be obvious to those skilled in the art that changes and modifications may be made without departing from the spirit and scope of the invention. The matter set forth in the foregoing description and accompanying drawings is offered by way of illustration only and not as a limitation.

The invention claimed is:

1. A method for preparing tumor-infiltrating lymphocytes (TILs) in vitro, the method comprising:

(1) providing an initial cell population containing TILs from a sample, wherein the number of TILs in the initial cell population is n0 wherein n0 ranges from 1,000 to 50,000;

(2) pre-treating the initial cell population, the pretreatment comprising culturing the initial cell population with IL7, IL15 and IL21 for 6 hours to 36 hours, to obtain a pretreated initial cell population, wherein each of IL7, IL15, and IL21 has a concentration ranging from 10 ng/ml to 100 μg/ml;

(3) co-culturing the pretreated initial cell population, with first feeder cells in a first culture medium for a first period of 7 days to 16 days, to obtain a first expanded cell population, wherein the first culture medium comprises (i) one or more cytokines selected from the group consisting of IL2, IL7, IL15, and IL21, and (ii) one or more antibodies selected from the group consisting of an anti-CD3 antibody or fragments thereof, an anti-41BB antibody or fragments thereof, an anti-OX40 antibody or fragments thereof, and an anti-PD-1 antibody or fragments thereof, wherein the number of TILs in the first expanded cell population is n1, wherein n1/n0 ranges from 1000 to 10,000, and n1 is at least $1\times10^7$; and (4) co-culturing the first expanded cell population with second feeder cells in a second culture medium for a second period of 10 days to 16 days, to obtain an expanded TIL population, wherein the second culture medium comprises one or more antibodies selected from the group consisting of an anti-CD3 antibody or fragments thereof, and an anti-CD28 antibody or fragments thereof, wherein the number of TILs in the expanded TIL population is n2, wherein n2/n1 ranges from 4000 to 10,000, and n2 is at least $1\times10^{10}$.

2. The method of claim 1, wherein the sample is a tumor sample.

3. The method of claim 2, wherein the tumor sample is from a solid tumor.

4. The method of claim 3, wherein the solid tumor is lung cancer, cervical cancer, ovarian cancer, or melanoma.

5. The method of claim 1, wherein the sample has a weight ranging from 0.01 g to 0.5 g.

6. The method of claim 1, wherein in step (1), the sample is dissociated with a dissociation solution to obtain the initial cell population, wherein the dissociation solution comprises an isotonic solution comprising collagenase II, collagenase IV, DNase, and hyaluronidase.

7. The method of claim 1, wherein the second culture medium comprises microbeads coated with one or more antibodies selected from the group consisting of an anti-CD3 antibody or fragments thereof, and an anti-CD28 antibody or fragments thereof.

8. The method of claim 1, wherein the first feeder cells and the second feeder cells are antigen presenting cells.

9. The method of claim 1, wherein the first feeder cells and the second feeder cells are peripheral blood mononuclear cells (PBMCs).

* * * * *